US012661091B2

(12) United States Patent
Bellamkonda et al.

(10) Patent No.: US 12,661,091 B2
(45) Date of Patent: Jun. 23, 2026

(54) METHODS AND APPARATUSES FOR MODIFYING THE LOCATION OF AN ULTRASOUND IMAGING PLANE

(71) Applicant: BFLY OPERATIONS, INC., Burlington, MA (US)

(72) Inventors: Kirthi Bellamkonda, New Haven, CT (US); Karl Thiele, St. Petersburg, FL (US); Abraham Neben, Guilford, CT (US); Billy Byungsoo Roh, New York, NY (US); David Elgena, Jersey City, NJ (US)

(73) Assignee: BFLY Operations, Inc., Burlington, MA (US)

( * ) Notice: Subject to any disclaimer, the term of this patent is extended or adjusted under 35 U.S.C. 154(b) by 0 days.

(21) Appl. No.: 17/137,787

(22) Filed: Dec. 30, 2020

(65) Prior Publication Data

US 2021/0196237 A1     Jul. 1, 2021

Related U.S. Application Data

(60) Provisional application No. 62/955,589, filed on Dec. 31, 2019.

(51) Int. Cl.
A61B 8/00          (2006.01)
A61B 8/08          (2006.01)

(52) U.S. Cl.
CPC ............ A61B 8/523 (2013.01); A61B 8/0841 (2013.01); A61B 8/461 (2013.01); A61B 8/467 (2013.01)

(58) Field of Classification Search
CPC ....... A61B 8/523; A61B 8/0841; A61B 8/461; A61B 8/467; A61B 8/463; A61B 8/0891
See application file for complete search history.

(56) References Cited

U.S. PATENT DOCUMENTS 5,891,039 A * 4/1999 Bonnefous ............... A61B 8/06
                                                              600/465
6,019,724 A    2/2000 Gronningsaeter et al.
                         (Continued)

FOREIGN PATENT DOCUMENTS

JP       2006006686 A  *  1/2006
WO     2019/016343 A1     1/2019

OTHER PUBLICATIONS

JP2006006686 English Translation, 2006 (Year: 2006).*
(Continued)

*Primary Examiner* — Adil Partap S Virk

(57)          ABSTRACT
Aspects of the technology described herein related to modifying the location of an ultrasound imaging plane. Some embodiments include modifying the location of the ultrasound imaging plane based on a user selection. For example, some embodiments include receiving the user selection through a graphical user interface (GUI) that includes an ultrasound imaging plane indicator, where the ultrasound imaging plane indicator indicates the location of the ultrasound imaging plane. As another example, some embodiments include receiving the user selection by detecting tilts, taps, or voice commands. Some embodiments include automatically modifying the location of the ultrasound imaging plane. Some embodiments include modifying the location of the ultrasound imaging plane during biplane imaging.

17 Claims, 19 Drawing Sheets

(56) References Cited

U.S. PATENT DOCUMENTS

| | | | | |
|---|---|---|---|---|
| 6,464,642 | B1 * | 10/2002 | Kawagishi | A61B 8/14 |
| | | | | 128/916 |
| D846,128 | S | 4/2019 | de Jonge et al. | |
| D846,749 | S | 4/2019 | de Jonge et al. | |
| D876,636 | S | 2/2020 | de Jonge et al. | |
| D881,224 | S | 4/2020 | Elgena et al. | |
| D881,225 | S | 4/2020 | Elgena et al. | |
| D881,226 | S | 4/2020 | Elgena et al. | |
| D881,227 | S | 4/2020 | Elgena et al. | |
| D881,919 | S | 4/2020 | Elgena et al. | |
| D885,427 | S | 5/2020 | Elgena et al. | |
| D885,428 | S | 5/2020 | Elgena et al. | |
| D887,439 | S | 6/2020 | Elgena et al. | |
| D887,850 | S | 6/2020 | Elgena | |
| D888,094 | S | 6/2020 | Elgena | |
| 10,667,790 | B2 * | 6/2020 | Chiang | A61B 8/468 |
| 10,702,242 | B2 | 7/2020 | de Jonge et al. | |
| 10,709,415 | B2 * | 7/2020 | Neben | A61B 8/54 |
| D903,694 | S | 12/2020 | Elgena et al. | |
| D903,709 | S | 12/2020 | Elgena | |
| 10,856,840 | B2 | 12/2020 | Rothberg et al. | |
| 2003/0060710 | A1 * | 3/2003 | Salgo | G01S 15/8925 |
| | | | | 600/443 |
| 2003/0149366 | A1 * | 8/2003 | Stringer | A61B 8/42 |
| | | | | 600/464 |
| 2003/0195421 | A1 * | 10/2003 | Demers | G01S 15/8993 |
| | | | | 600/437 |
| 2004/0015080 | A1 * | 1/2004 | Kelly | A61B 8/406 |
| | | | | 600/459 |
| 2004/0111028 | A1 * | 6/2004 | Abe | A61B 8/463 |
| | | | | 600/437 |
| 2004/0210138 | A1 * | 10/2004 | Murashita | G01S 7/52074 |
| | | | | 600/443 |
| 2007/0156050 | A1 | 7/2007 | Barnes et al. | |
| 2007/0167809 | A1 * | 7/2007 | Dala-Krishna | A61B 8/13 |
| | | | | 600/459 |
| 2007/0276239 | A1 * | 11/2007 | Rafter | A61B 8/4483 |
| | | | | 600/437 |
| 2008/0051652 | A1 * | 2/2008 | Ichioka | A61B 8/08 |
| | | | | 600/437 |
| 2009/0136109 | A1 * | 5/2009 | Salgo | A61B 8/0858 |
| | | | | 600/443 |
| 2010/0121189 | A1 * | 5/2010 | Ma | A61B 8/463 |
| | | | | 600/437 |
| 2010/0240994 | A1 | 9/2010 | Zheng | |
| 2010/0312120 | A1 * | 12/2010 | Meier | A61B 8/00 |
| | | | | 600/459 |
| 2011/0055447 | A1 | 3/2011 | Costa | |
| 2011/0079082 | A1 * | 4/2011 | Yoo | A61B 8/483 |
| | | | | 73/632 |
| 2011/0257505 | A1 * | 10/2011 | Suri | G16H 50/30 |
| | | | | 600/443 |
| 2012/0245465 | A1 | 9/2012 | Hansegard et al. | |
| 2013/0158405 | A1 * | 6/2013 | Bagge | A61B 8/4488 |
| | | | | 600/447 |
| 2013/0303915 | A1 * | 11/2013 | Barnard | A61B 8/5207 |
| | | | | 600/449 |
| 2014/0013849 | A1 | 1/2014 | Gerard et al. | |
| 2014/0058266 | A1 * | 2/2014 | Call | A61B 8/14 |
| | | | | 600/443 |
| 2014/0369583 | A1 * | 12/2014 | Toji | G06T 7/0014 |
| | | | | 382/131 |
| 2014/0378837 | A1 * | 12/2014 | Fujiwara | A61B 8/463 |
| | | | | 600/443 |
| 2015/0042657 | A1 * | 2/2015 | Smith-Casem | G06T 19/00 |
| | | | | 345/427 |
| 2015/0190119 | A1 * | 7/2015 | Park | A61B 8/5223 |
| | | | | 600/440 |
| 2015/0272546 | A1 | 10/2015 | Cheon et al. | |
| 2015/0305718 | A1 * | 10/2015 | Ogasawara | A61B 8/54 |
| | | | | 600/440 |
| 2016/0015368 | A1 * | 1/2016 | Poland | A61B 8/4405 |
| | | | | 600/447 |
| 2016/0100821 | A1 * | 4/2016 | Eggers | A61B 8/54 |
| | | | | 600/424 |
| 2016/0146914 | A1 * | 5/2016 | Nitta | G01R 33/4835 |
| | | | | 324/309 |
| 2016/0199029 | A1 * | 7/2016 | Struijk | A61B 8/02 |
| | | | | 600/443 |
| 2017/0020559 | A1 | 1/2017 | Srinivasan et al. | |
| 2017/0036097 | A1 | 2/2017 | Durbin | |
| 2017/0285156 | A1 * | 10/2017 | Yigang | A61B 8/00 |
| 2018/0279996 | A1 * | 10/2018 | Cox | A61B 8/466 |
| 2018/0296190 | A1 * | 10/2018 | Susumu | A61B 8/5269 |
| 2019/0015069 | A1 * | 1/2019 | Heller | A61B 8/0858 |
| 2019/0015076 | A1 * | 1/2019 | Rouet | A61B 8/483 |
| 2019/0142388 | A1 | 5/2019 | Gonyeau et al. | |
| 2019/0307428 | A1 | 10/2019 | Silberman et al. | |
| 2020/0129151 | A1 | 4/2020 | Neben et al. | |
| 2020/0129155 | A1 | 4/2020 | Elgena et al. | |
| 2020/0129156 | A1 | 4/2020 | Elgena et al. | |
| 2020/0174118 | A1 * | 6/2020 | Tadross | A61B 8/0891 |
| 2020/0174119 | A1 * | 6/2020 | Tadross | G01S 7/52071 |
| 2020/0205671 | A1 * | 7/2020 | Tashiro | A61B 8/463 |
| 2020/0214672 | A1 | 7/2020 | de Jonge et al. | |
| 2020/0214682 | A1 | 7/2020 | Zaslavsky et al. | |
| 2020/0253585 | A1 | 8/2020 | Neben et al. | |
| 2020/0261054 | A1 | 8/2020 | Silberman et al. | |
| 2020/0320694 | A1 | 10/2020 | Howell et al. | |
| 2020/0359990 | A1 * | 11/2020 | Poland | A61B 8/463 |
| 2020/0390419 | A1 | 12/2020 | Neben et al. | |
| 2020/0405271 | A1 | 12/2020 | Chiu et al. | |
| 2021/0015456 | A1 * | 1/2021 | Chiang | A61B 8/0883 |
| 2021/0290203 | A1 * | 9/2021 | Xie | A61B 8/0883 |
| 2021/0321986 | A1 * | 10/2021 | Clark | G01S 7/52071 |
| 2022/0233171 | A1 * | 7/2022 | Johnson | A61B 8/585 |

OTHER PUBLICATIONS

International Search Report and Written Opinion mailed Mar. 30, 2021 in connection with International Application No. PCT/US2020/067461.

PCT/US2020/067461, Mar. 30, 2021, International Search Report and Written Opinion.

Extended European Search Report issued in corresponding European Patent Application No. 20909811.0, dated Dec. 12, 2023 (10 pages).

* cited by examiner

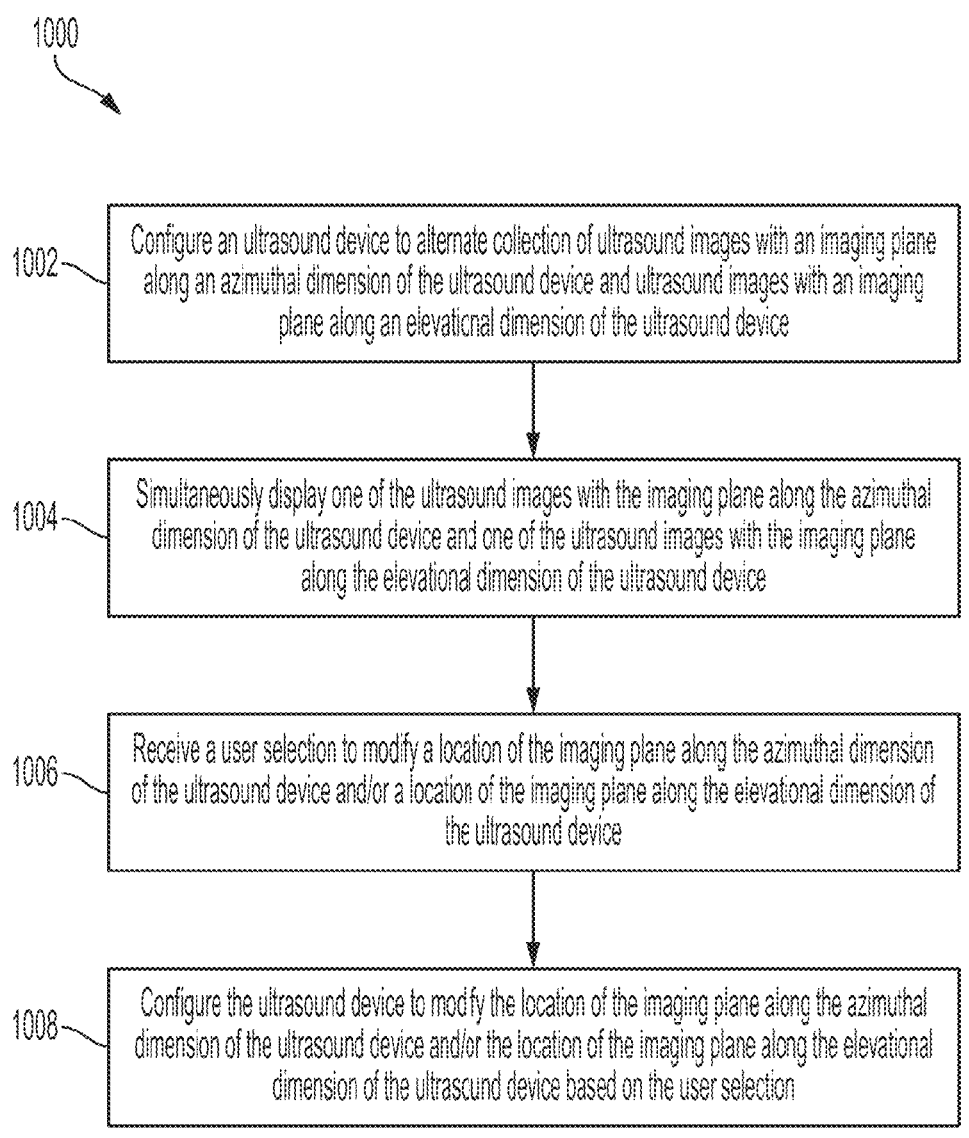

1000

1002 — Configure an ultrasound device to alternate collection of ultrasound images with an imaging plane along an azimuthal dimension of the ultrasound device and ultrasound images with an imaging plane along an elevational dimension of the ultrasound device 1004 — Simultaneously display one of the ultrasound images with the imaging plane along the azimuthal dimension of the ultrasound device and one of the ultrasound images with the imaging plane along the elevational dimension of the ultrasound device 1006 — Receive a user selection to modify a location of the imaging plane along the azimuthal dimension of the ultrasound device and/or a location of the imaging plane along the elevational dimension of the ultrasound device 1008 — Configure the ultrasound device to modify the location of the imaging plane along the azimuthal dimension of the ultrasound device and/or the location of the imaging plane along the elevational dimension of the ultrasound device based on the user selection

FIG. 10

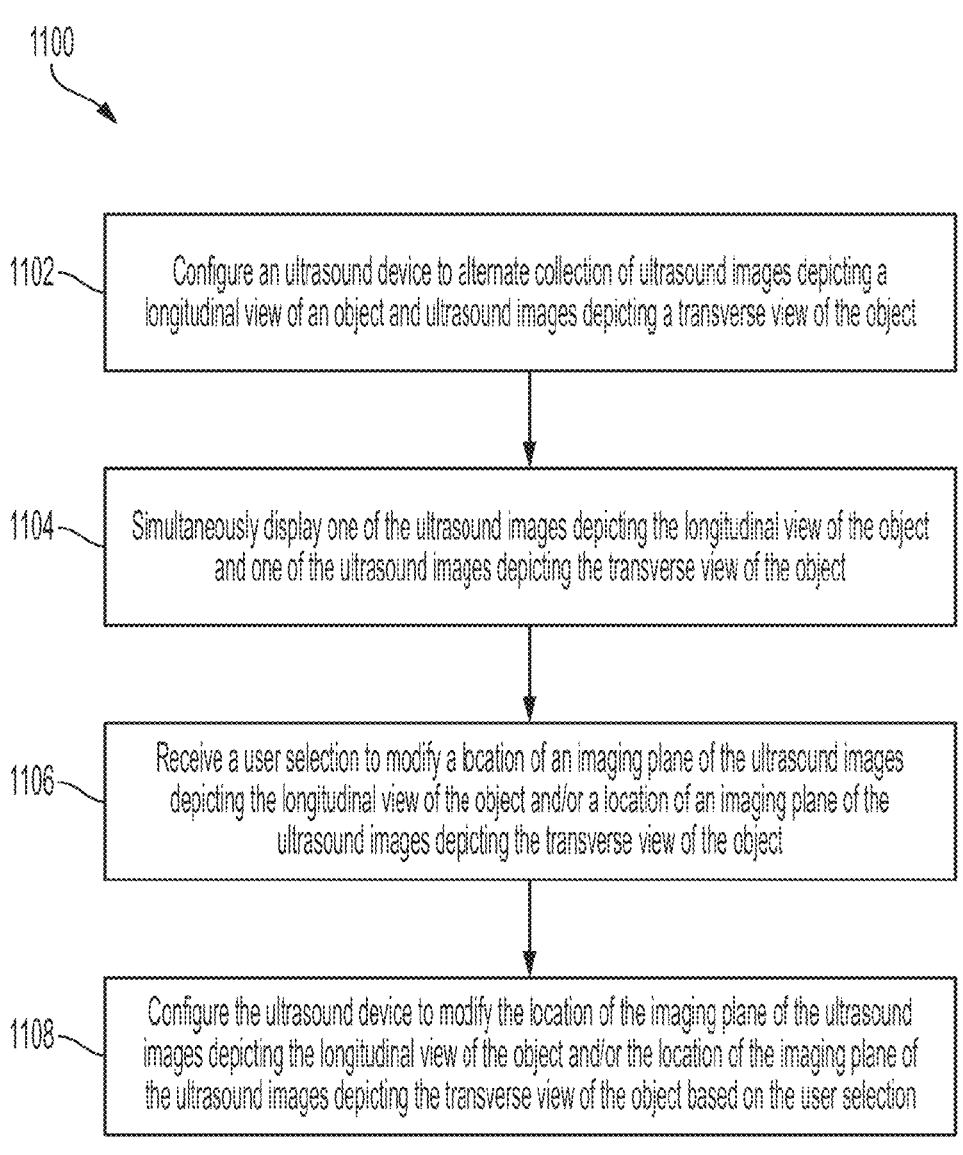

1100

1102 — Configure an ultrasound device to alternate collection of ultrasound images depicting a longitudinal view of an object and ultrasound images depicting a transverse view of the object 1104 — Simultaneously display one of the ultrasound images depicting the longitudinal view of the object and one of the ultrasound images depicting the transverse view of the object 1106 — Receive a user selection to modify a location of an imaging plane of the ultrasound images depicting the longitudinal view of the object and/or a location of an imaging plane of the ultrasound images depicting the transverse view of the object 1108 — Configure the ultrasound device to modify the location of the imaging plane of the ultrasound images depicting the longitudinal view of the object and/or the location of the imaging plane of the ultrasound images depicting the transverse view of the object based on the user selection

FIG. 11

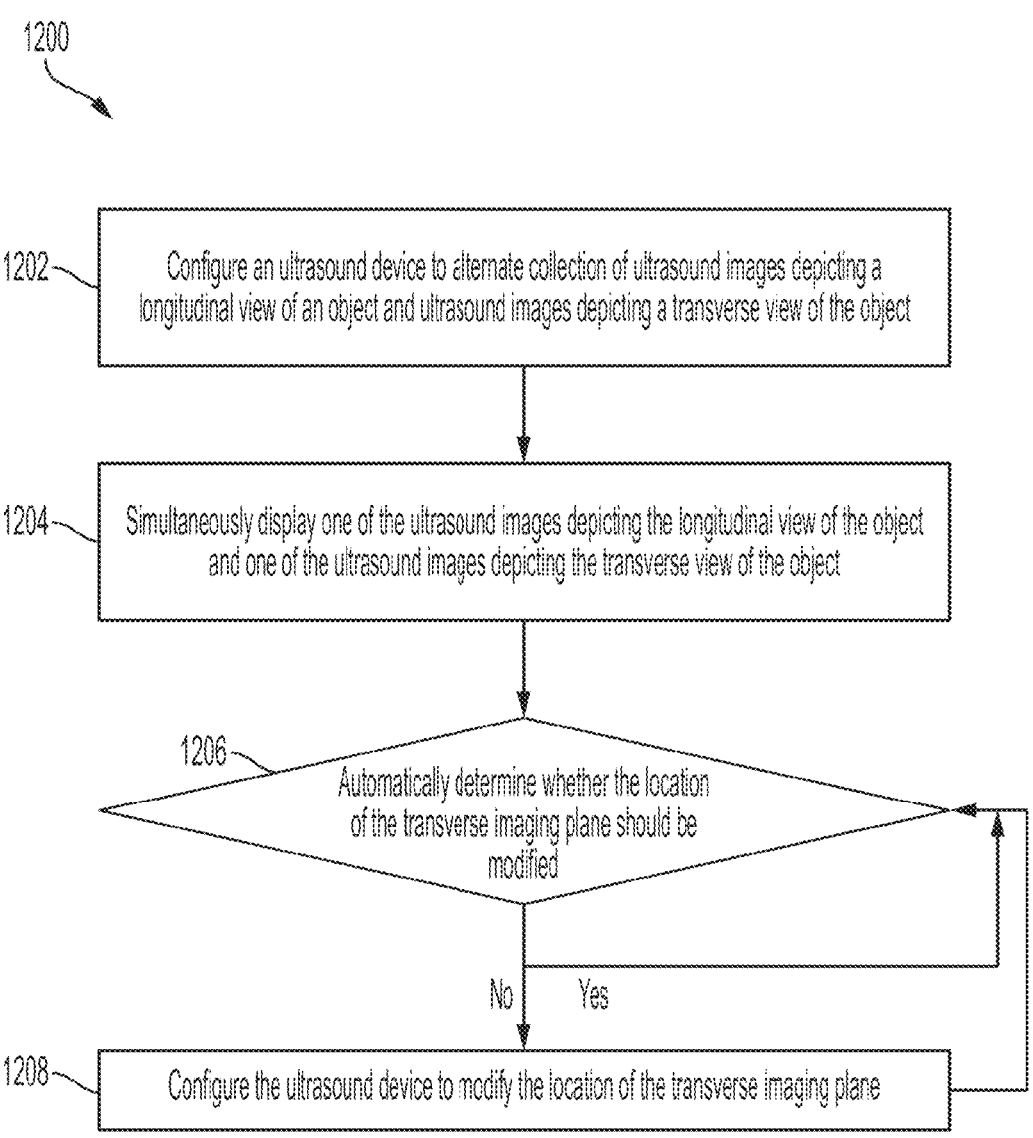

1200

1202 — Configure an ultrasound device to alternate collection of ultrasound images depicting a longitudinal view of an object and ultrasound images depicting a transverse view of the object 1204 — Simultaneously display one of the ultrasound images depicting the longitudinal view of the object and one of the ultrasound images depicting the transverse view of the object 1206 — Automatically determine whether the location of the transverse imaging plane should be modified No    Yes 1208 — Configure the ultrasound device to modify the location of the transverse imaging plane

FIG. 12

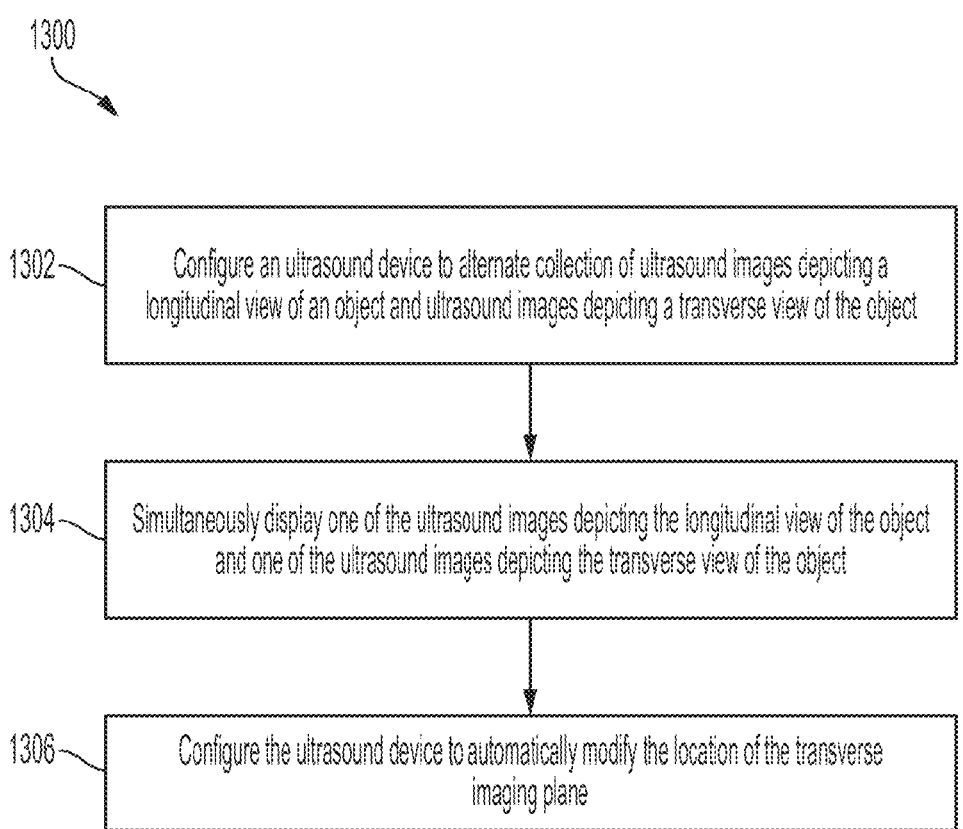

1300

1302 — Configure an ultrasound device to alternate collection of ultrasound images depicting a longitudinal view of an object and ultrasound images depicting a transverse view of the object 1304 — Simultaneously display one of the ultrasound images depicting the longitudinal view of the object and one of the ultrasound images depicting the transverse view of the object 1306 — Configure the ultrasound device to automatically modify the location of the transverse imaging plane

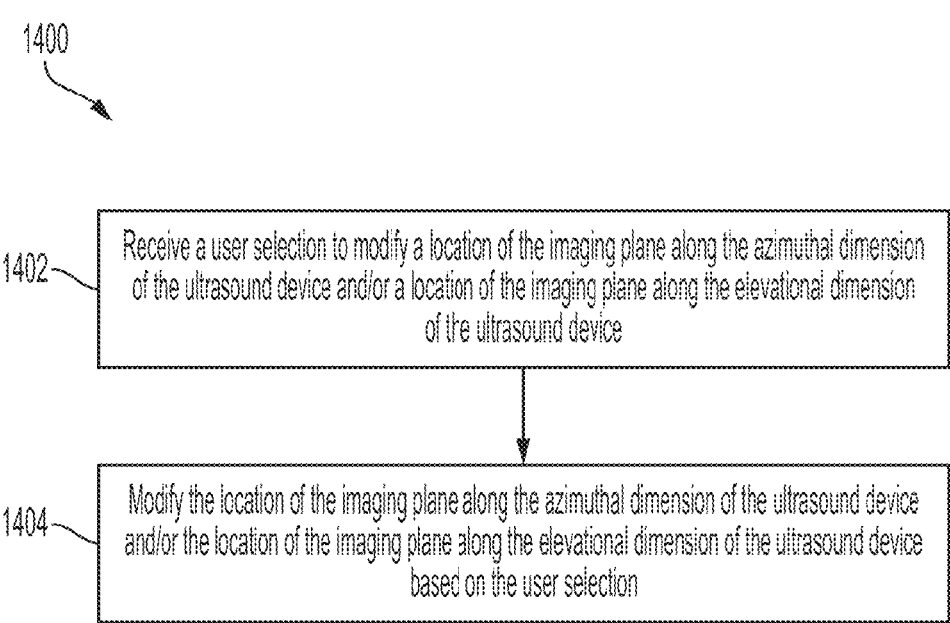

1402

Receive a user selection to modify a location of the imaging plane along the azimuthal dimension of the ultrasound device and/or a location of the imaging plane along the elevational dimension of the ultrasound device

1404

Modify the location of the imaging plane along the azimuthal dimension of the ultrasound device and/or the location of the imaging plane along the elevational dimension of the ultrasound device based on the user selection

FIG. 14

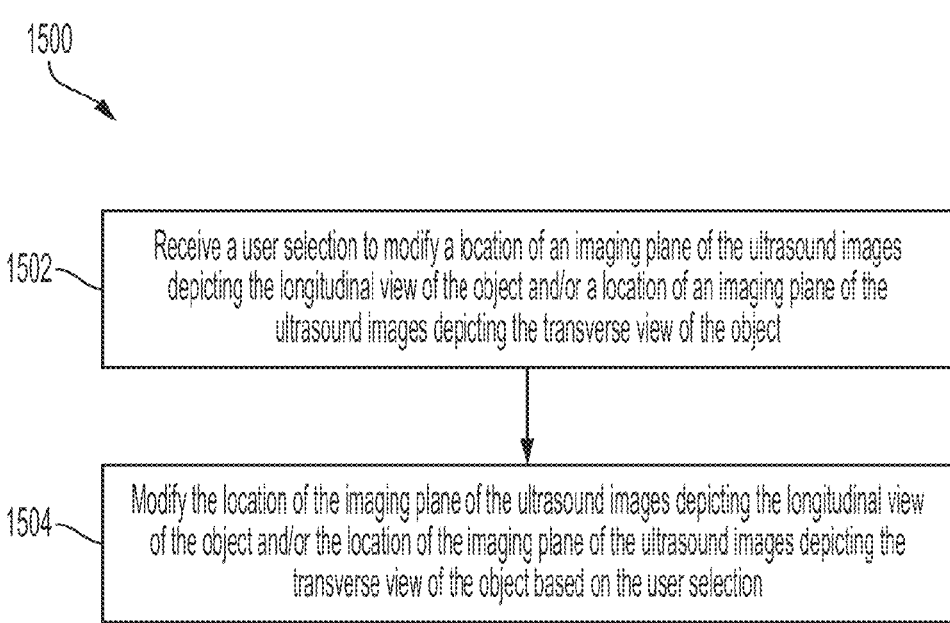

1500

1502— Receive a user selection to modify a location of an imaging plane of the ultrasound images depicting the longitudinal view of the object and/or a location of an imaging plane of the ultrasound images depicting the transverse view of the object 1504— Modify the location of the imaging plane of the ultrasound images depicting the longitudinal view of the object and/or the location of the imaging plane of the ultrasound images depicting the transverse view of the object based on the user selection

1602 — Automatically determine whether the location of the transverse imaging plane should be modified No    Yes 1604 — Configure the ultrasound device to modify the location of the transverse imaging plane

METHODS AND APPARATUSES FOR MODIFYING THE LOCATION OF AN ULTRASOUND IMAGING PLANE

CROSS-REFERENCE TO RELATED APPLICATIONS

The present application claims the benefit under 35 U.S.C. § 119(e) of U.S. Patent Application Ser. No. 62/955,589, filed Dec. 31, 2019, and entitled "METHODS AND APPARATUSES FOR MODIFYING THE LOCATION OF AN ULTRASOUND IMAGING PLANE," which is hereby incorporated by reference herein in its entirety.

FIELD

Generally, the aspects of the technology described herein relate to collection of ultrasound images. Some aspects relate to methods and apparatuses for modifying the location of an ultrasound imaging plane.

BACKGROUND

Ultrasound probes may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect, an apparatus includes a processing device in operative communication with an ultrasound device, the processing device configured to receive a user selection to modify a location of the first ultrasound imaging plane, where the processing device is configured, when receiving the user selection, to receive the user selection through a graphical user interface (GUI) displayed by the processing device and including a first ultrasound imaging plane indicator. The first ultrasound imaging plane indicator indicates the location of the first ultrasound imaging plane. The processing device is configured to configure the ultrasound device to modify the location of the first ultrasound imaging plane based on the user selection.

In some embodiments, the processing device is further configured to simultaneously display an ultrasound image having the first ultrasound imaging plane and an ultrasound image having a second ultrasound imaging plane. In some embodiments, the processing device is further configured to display the first ultrasound imaging plane indicator superimposed on an ultrasound image with a second ultrasound imaging plane or adjacent to the ultrasound image having the second ultrasound imaging plane. In some embodiments, the first ultrasound imaging plane indicator indicates where the first ultrasound imaging plane intersects the second ultrasound imaging plane. In some embodiments, the first ultrasound imaging plane intersects the second ultrasound imaging plane at a real-world location corresponding to a location of the first ultrasound imaging plane indicator in the ultrasound image having the second ultrasound imaging plane.

In some embodiments, the processing device is configured, when receiving the user selection to modify the position of the first ultrasound imaging plane, to detect a dragging movement on the first ultrasound imaging plane indicator or on the ultrasound image having the second ultrasound imaging plane. In some embodiments, the processing device is configured, when receiving the user selection to modify the position of the first ultrasound imaging plane, to receive a selection of a location on the ultrasound image having the second ultrasound imaging plane.

In some embodiments, the processing device is further configured to display a second ultrasound imaging plane indicator superimposed on the ultrasound image having the first ultrasound imaging plane or adjacent to the ultrasound image having the first ultrasound imaging plane. In some embodiments, the second ultrasound imaging plane indicator of indicates where the second ultrasound imaging plane intersects the first ultrasound imaging plane. In some embodiments, the second ultrasound imaging plane intersects the first ultrasound imaging plane at a real-world location corresponding to a location of the second ultrasound imaging plane indicator in the ultrasound image having the first ultrasound imaging plane. In some embodiments, the second ultrasound imaging plane intersects the first ultrasound imaging plane at a real-world location corresponding to a location of the second ultrasound imaging plane indicator in the ultrasound image having the first ultrasound imaging plane.

In some embodiments, the processing device is further configured to display a three-dimensional visualization of the location of the first ultrasound imaging plane.

In some embodiments, the processing device does not enable a user to modify a location of the second ultrasound imaging plane. In some embodiments, the processing device is configured to display the first ultrasound imaging plane indicator and the second ultrasound imaging plane indicator with different formats.

According to another aspect, an apparatus includes a processing device in operative communication with an ultrasound device, the processing device configured to receive a user selection to modify a location of a first ultrasound imaging plane by detecting a tilt of the processing device; receiving, from the ultrasound device, an indication of a detection of a tilt of the ultrasound device; receiving, from the ultrasound device, an indication of a detection of one or more taps on an exterior of the ultrasound device; and/or receiving a user voice command. The processing device is configured to configure the ultrasound device to modify the location of the first ultrasound imaging plane based on the user selection.

In some embodiments of any of the above aspects, the processing device is configured to receive the user selection to modify the location of the first ultrasound imaging plane and to configure the ultrasound the ultrasound device to modify the location of the first ultrasound imaging plane during biplane imaging. In some embodiments of any of the above aspects, the processing device is configured to receive the user selection to modify the location of the first ultrasound imaging plane without receiving a user selection to change an ultrasound imaging mode or an ultrasound imaging preset.

In some embodiments of any of the above aspects, the processing device is further configured to configure the ultrasound device to alternate collection of ultrasound images with the first ultrasound imaging plane and ultrasound images with a second ultrasound imaging plane. In some embodiments of any of the above aspects, the processing device is configured, when configuring the ultrasound device to alternate collection of the ultrasound images with the first ultrasound imaging plane and the ultrasound images with the second ultrasound imaging plane, to configure the ultrasound device to collect ultrasound images such that a time period between collection of successive ultrasound images is in the range of approximately $\frac{1}{30}$-$\frac{1}{15}$ seconds. In some embodiments of any of the above aspects, the processing device is configured, when configuring the ultrasound device to alternate collection of the ultrasound images with the first ultrasound imaging plane and the ultrasound images with the second ultrasound imaging plane, to configure the ultrasound device to collect one ultrasound image having the first ultrasound imaging plane, then collect one ultrasound image having the second ultrasound imaging plane, and then collect one ultrasound image having the first ultrasound imaging plane. In some embodiments of any of the above aspects, the processing device is configured, when configuring the ultrasound device to alternate collection of the ultrasound images with the first ultrasound imaging plane and the ultrasound images with the second ultrasound imaging plane, to configure the ultrasound device to collect one or more ultrasound images with the first ultrasound imaging plane, then collect one or more ultrasound images with the second ultrasound imaging plane, then collect one or more ultrasound images with the first ultrasound imaging plane. In some embodiments of any of the above aspects, the processing device is configured, when configuring the ultrasound device to alternate collection of the ultrasound images with the first ultrasound imaging plane and the ultrasound images with the second ultrasound imaging plane, to configure the ultrasound device to collect the ultrasound images with the first ultrasound imaging plane using a first aperture and to collect the ultrasound images with the second ultrasound imaging plane using a second aperture. In some embodiments of any of the above aspects, the first ultrasound imaging plane is along an elevational dimension of the ultrasound device, the second ultrasound imaging plane is along an azimuthal dimension of the ultrasound device, the first aperture has a long dimension along the elevational dimension of the ultrasound device, and the second aperture has a long dimension along the azimuthal dimension of the ultrasound device. In some embodiments of any of the above aspects, the processing device is configured, when configuring the ultrasound device to alternate collection of the ultrasound images with the first ultrasound imaging plane and the ultrasound images with the second ultrasound imaging plane, to configure the ultrasound device to collect the ultrasound images with the first ultrasound imaging plane using a first set of beamforming parameters and to collect the ultrasound images with the second ultrasound imaging plane using a second set of beamforming parameters.

In some embodiments of any of the above aspects, a user does not rotate the ultrasound device when the ultrasound device is alternating collection of the ultrasound images with the first ultrasound imaging plane and the ultrasound images with the second ultrasound imaging plane.

In some embodiments of any of the above aspects, the second ultrasound imaging plane is along an elevational dimension of the ultrasound device. In some embodiments of any of the above aspects, the second ultrasound imaging plane is along an azimuthal dimension of the ultrasound device. In some embodiments of any of the above aspects, the first ultrasound imaging plane is along an elevational dimension of the ultrasound device. In some embodiments of any of the above aspects, the first ultrasound imaging plane is along an azimuthal dimension of the ultrasound device.

In some embodiments of any of the above aspects, the processing device does not enable a user to modify a location of the second ultrasound imaging plane. In some embodiments of any of the above aspects, the processing device is further configured to receive a user selection to modify a position of the second ultrasound imaging plane and configure the ultrasound device to modify the position of the second ultrasound imaging plane based on the user selection.

According to another aspect, an apparatus includes a processing device in operative communication with an ultrasound device, the processing device configured to configure the ultrasound device to automatically modify the location of an ultrasound imaging plane.

In some embodiments, the processing device is configured to configure the ultrasound device to automatically modify the location of the ultrasound imaging plane during biplane imaging. In some embodiments, the processing device is further configured to automatically determine whether the ultrasound imaging plane should be modified, and the processing device is configured to configure the ultrasound device to automatically modify the location of the ultrasound imaging plane based on automatically determining whether the ultrasound imaging plane should be modified. In some embodiments, the processing device is configured, when automatically determining whether the ultrasound imaging plane should be modified, to use a statistical model to determine whether the imaging plane should be modified. In some embodiments, the processing device is configured, when using the statistical model to determine whether the imaging plane should be modified, to determine whether an ultrasound image substantially depicts a tip of an object. In some embodiments, the processing device is configured, when configuring the ultrasound device to automatically modify the location of the ultrasound imaging plane, to shift the location of the ultrasound imaging plane by an increment in a direction of an insertion of the object. In some embodiments, the object is a needle. In some embodiments, the ultrasound image depicts a transverse view of the object. In some embodiments, the processing device is further configured to automatically determine the direction of the insertion of the object. In some embodiments, the processing device is further configured to receive an input of the direction of the insertion.

In some embodiments, the processing device is configured, when configuring the ultrasound device to automatically modify the location of the ultrasound imaging plane, to configure the ultrasound device to automatically modify the location of the ultrasound imaging plane at a fixed speed. In some embodiments, the fixed speed is user-controllable.

Some aspects include a method of performing the above functions of the processing device. Some aspects include at least one non-transitory computer-readable storage medium storing processor-executable instructions that, when executed by at least one processor on a processing device in operative communication with an ultrasound device, cause the at least one processor to perform the above functions of the processing device.

Some aspects include an ultrasound device configured to perform the above functions of the processing device, and rather than the processing device configuring the ultrasound device, the ultrasound device configures itself. Some aspects include a method of performing, by an ultrasound device, the above functions of the processing device. Some aspects include at least one non-transitory computer-readable storage medium storing processor-executable instructions that, when executed by at least one processor on an ultrasound device, cause the at least one processor to perform the above functions of the processing device.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIG. 10 illustrates a process for biplane imaging, in accordance with certain embodiments described herein;

FIG. 11 illustrates another process for biplane imaging, in accordance with certain embodiments described herein;

FIG. 12 illustrates another process for biplane imaging, in accordance with certain embodiments described herein; and FIG. 13 illustrates another process for biplane imaging, in accordance with certain embodiments described herein; and FIG. 14 illustrates another process for biplane imaging, in accordance with certain embodiments described herein; and FIG. 15 illustrates another process for biplane imaging, in accordance with certain embodiments described herein; and

6

Figure 16:
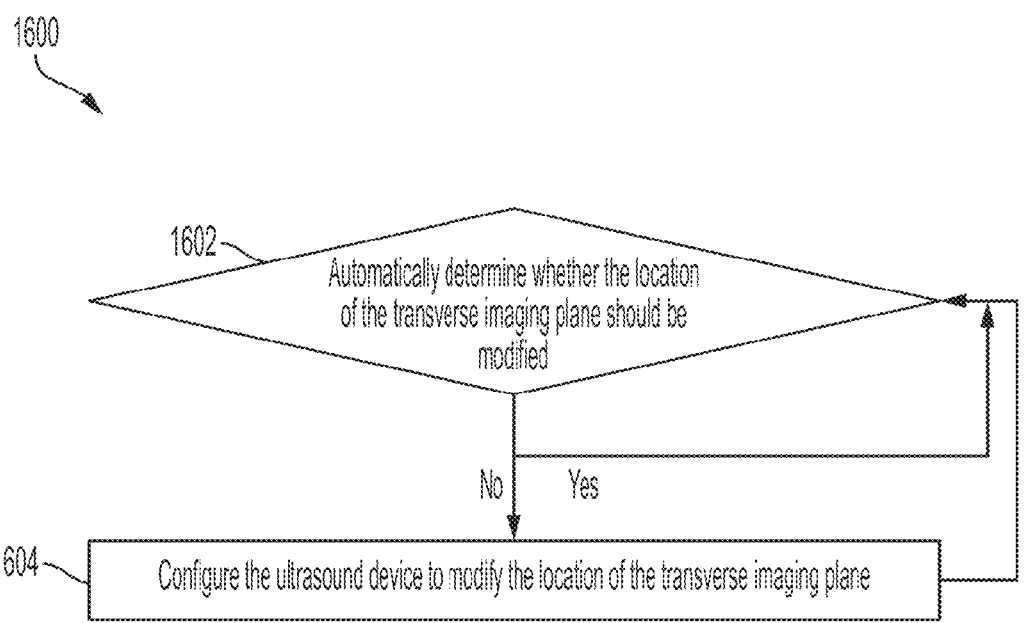
Figure 17:
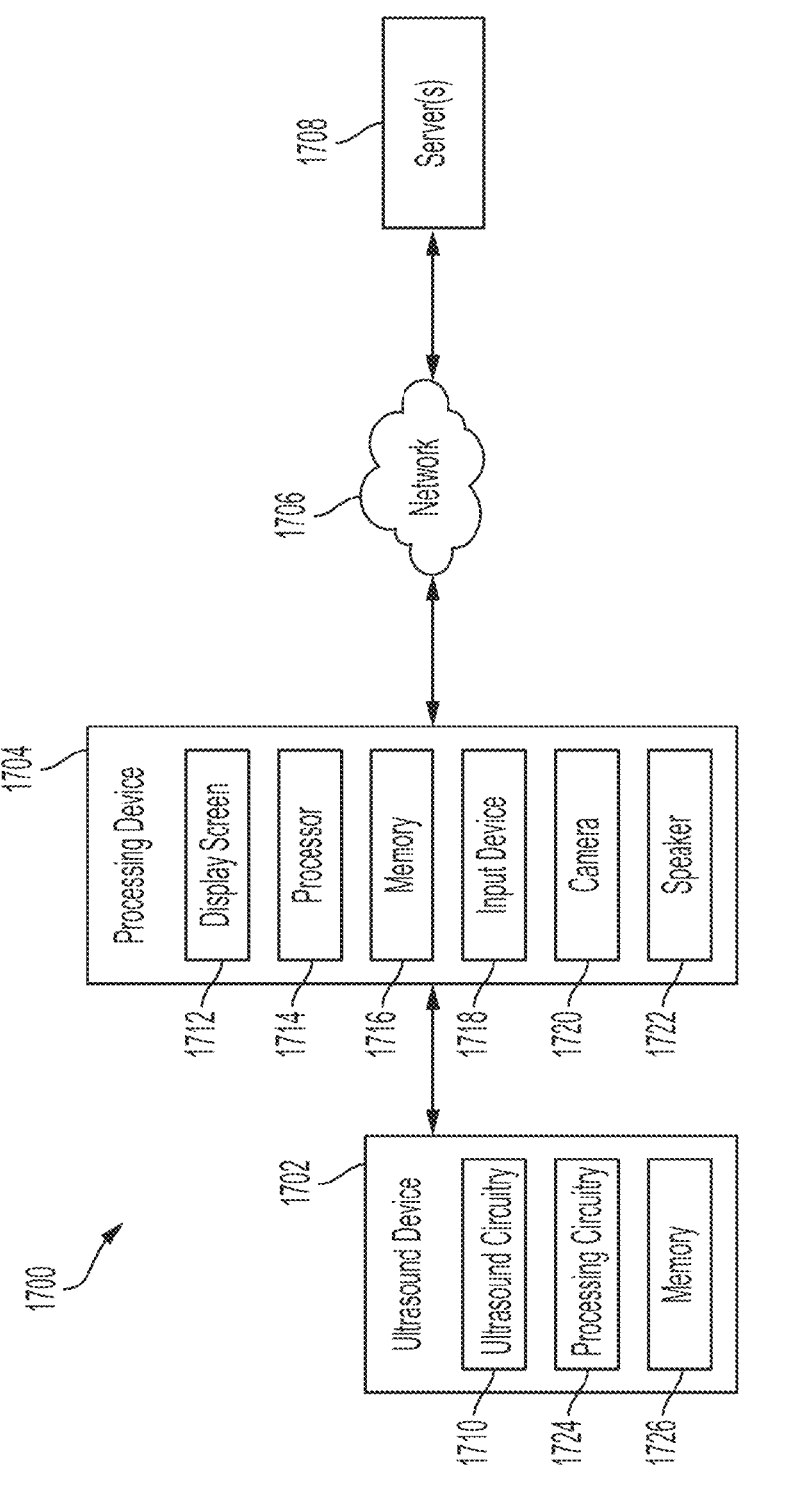

FIG. 16 illustrates another process for biplane imaging, in accordance with certain embodiments described herein; and FIG. 17 illustrates a schematic block diagram of an example ultrasound system upon which various aspects of the technology described herein may be practiced.

DETAILED DESCRIPTION

Certain medical procedures (e.g., biopsies and aspirations) may include insertion of a needle into a patient. Ultrasound imaging of the patient may be performed during insertion of the needle so that the medical professional inserting the needle may monitor the needle and reduce the chance of accidentally injuring nerves, vessels, and other anatomical structures during the insertion of the needle. Biplane imaging, in which an ultrasound device collects ultrasound images with two imaging planes, may enable a medical professional who is inserting the needle to view the needle from a longitudinal view and a transverse view. It may be helpful to be able to simultaneously view ultrasound images with the longitudinal view and ultrasound images with the transverse view to ensure that the needle is being inserted into the subject safely and correctly (e.g., into the correct portion of the subject's anatomy, without piercing other portions of the subject's anatomy). This application describes technology for biplane imaging in which an ultrasound device may collect ultrasound images with two different imaging planes, without a user needing to rotate the ultrasound device, and simultaneously display both types of ultrasound images on a processing device in operative communication with the ultrasound device. Biplane imaging without a user needing to rotate the ultrasound device may be helpful for maintaining the region-of-interest within view of the ultrasound device.

In some embodiments, GUIs displaying two ultrasound images with two different imaging planes may include indicators of locations of imaging planes. For example, if there is one ultrasound image depicting a longitudinal view of a needle and another ultrasound image depicting a transverse view of the needle, the longitudinal ultrasound image may include an indicator the transverse imaging plane, such that the transverse imaging plane intersects the longitudinal imaging plane at a real-world location corresponding to the location of the transverse imaging plane indicator in the longitudinal ultrasound image. Such indicators may help a user to visualize and understand the locations of imaging planes may help to reduce user confusion in performing biplane imaging.

It may also be helpful to modify the position of one or both imaging planes used to collect the ultrasound images. For example, it may be helpful to modify the position of the imaging plane used to collect a transverse view of a needle as the needle is inserted further into the subject, such that the transverse imaging plane is located at the tip of the needle. This may help the user who is inserting the needle to ensure that as the needle is inserted toward the target portion of the subject's anatomy, the needle does not deviate right or left too much. This application describes embodiments of technology for modifying the location of imaging planes for biplane imaging, without a user needing to rotate the ultrasound device. The technology includes graphical user interfaces (GUIs) for enabling a user to control the location of an imaging plane, where the GUIs are displayed on a processing device in operative communication with the ultrasound device. In some embodiments, a user may control the location of the imaging plane using an indicator of the location of the imaging plane in a GUI (e.g., an indicator of the type described above). In a similar vein as above, using the indicators to modify the location of imaging planes may help a user to visualize and understand the locations of imaging planes and may help to reduce user confusion in performing biplane imaging.

The technology includes other methods for controlling the location of an imaging plane. In some embodiments, a user may control the location of imaging planes by tilting a processing device or an ultrasound device, by tapping the ultrasound device, or through voice commands. In some embodiments, the ultrasound device may be configured to automatically modify the location of an imaging plane. For example, in some embodiments, the ultrasound device may be configured to modify the location of an imaging plane based on whether or not ultrasound images collected by the ultrasound device ultrasound image depict the tip of an object such as a needle. As another example, in some embodiments, the ultrasound device may be configured to modify the location of an imaging plane at a fixed speed.

It should be appreciated that while this description focuses on biplane ultrasound imaging, the same methods and apparatuses may be applied to modifying the location of an ultrasound imaging plane when only one imaging plane is used.

It should also be appreciated that while this description focuses on ultrasound imaging of needles, the same description may apply to other objects that are inserted into patients for medical procedures, such as hookwires and T-bars for example. Additionally, biplane imaging may be useful for other applications besides insertion of objects into subjects, such as visualizing non-spherical structures. For example, multiplanar measurements of thyroid nodules may lead to more accurate volume estimation.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

Figure 1:
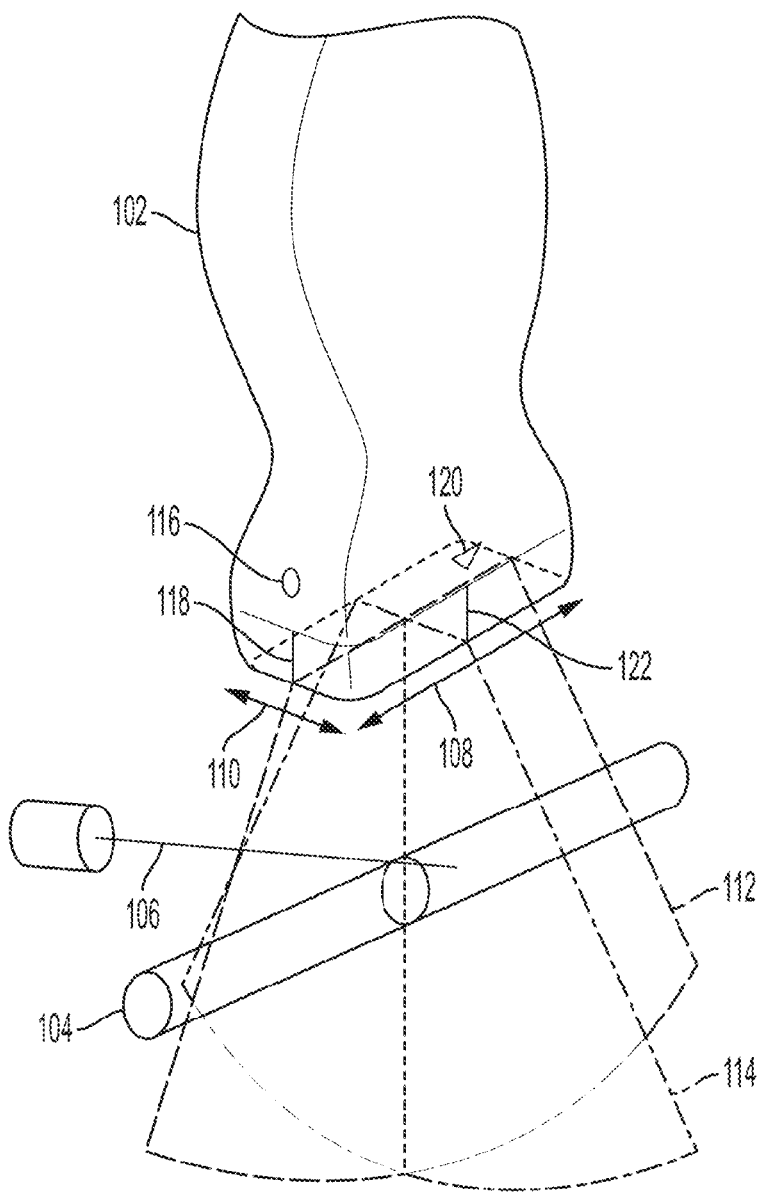
FIG. 1 illustrates a schematic diagram of an example of an ultrasound device imaging a needle being inserted into a subject, in accordance with certain embodiments described herein.

FIG. 1 illustrates a schematic diagram of an example of an ultrasound device 102 imaging a needle 106 being inserted into a vessel 104 (e.g., a blood vessel), in accordance with certain embodiments described herein. The ultrasound device 102 (more specifically, the transducer array, not shown, of the ultrasound device 102) includes an azimuthal dimension 108 and an elevational dimension 110. The azimuthal dimension 108 may be the dimension of the ultrasound transducer array that has more ultrasound transducers than the other dimension, which may be the elevational dimension 110. FIG. 1 further illustrates an imaging plane 112 along the azimuthal dimension 108 of the ultrasound device 102. The ultrasound device 102 may collect ultrasound data from and depict one or more ultrasound images of objects within the imaging plane 112. The ultrasound device 102 and the needle 106 are arranged such that the imaging plane 112 along the azimuthal dimension 108 of the ultrasound device 102 may capture a longitudinal view of the needle 106. In other words, a portion of the length of the needle 106 may be visible in ultrasound images generated based on data captured using the imaging plane 112. When the imaging plane 112 collects ultrasound images depicting a longitudinal view of the needle 106, it may be referred to as the longitudinal imaging plane 112. FIG. 1 further illustrates an imaging plane 114 along the elevational dimension 110 of the ultrasound device 102. The ultrasound device 102 may collect ultrasound data from and depict one or more ultrasound images of objects within the imaging plane 114. The ultrasound device 102 and the needle 106 are arranged such that the imaging plane 114 along the azimuthal dimension 108 of the ultrasound device 102 may capture a transverse view of the needle 106. In other words, the needle 106 may be visible as a point in ultrasound images generated based on data captured using the imaging plane 114. When the imaging plane 114 collects ultrasound images depicting a transverse view of the needle 106, it may be referred to as the transverse imaging plane 114.

The ultrasound device 102 includes a marker 116, a marker 118, a marker 120, and a marker 122. The marker 116 is disposed on a face of the ultrasound device 102 that is on one side of the azimuthal dimension 108 of the ultrasound device 102. The marker 116 may therefore mark one side of the azimuthal dimension 108 of the ultrasound device 102. The marker 120 is disposed on a face of the ultrasound device 102 that is on one side of the elevational dimension 110 of the ultrasound device 102. The marker 120 may therefore mark one side of the elevational dimension 110 of the ultrasound device 102. The marker 118 is disposed on the ultrasound device 102 such that the marker 118 is aligned approximately with a default location of the longitudinal imaging plane 112. The marker 122 is disposed on the ultrasound device 102 such that the marker 122 is aligned approximately with a default location of the transverse imaging plane 114.

As described above, it may be helpful for a user who is inserting the needle 106 to be able to simultaneously view ultrasound images collected with both the longitudinal imaging plane 112 and the transverse imaging plane 114 to ensure that the needle 106 is being inserted into the vessel 104 safely and correctly (e.g., into the correct portion of the subject's anatomy, without piercing other portions of the subject's anatomy). It may also be helpful for an operator of the ultrasound device 102 (who may be the same as the user who is inserting the needle 106) to be able to modify the position of the longitudinal imaging plane 112 and/or the transverse imaging plane 114. For example, it may be helpful to modify the position of the transverse imaging plane 114 as the needle 106 is inserted further into the vessel 104, such that the transverse imaging plane 114 is located at the tip of the needle 106. This may help the user who is inserting the needle 106 to ensure that as the needle 106 is inserted toward the target portion of the anatomy of the vessel 104, the needle 106 does not deviate right or left too much.

Figure 2:
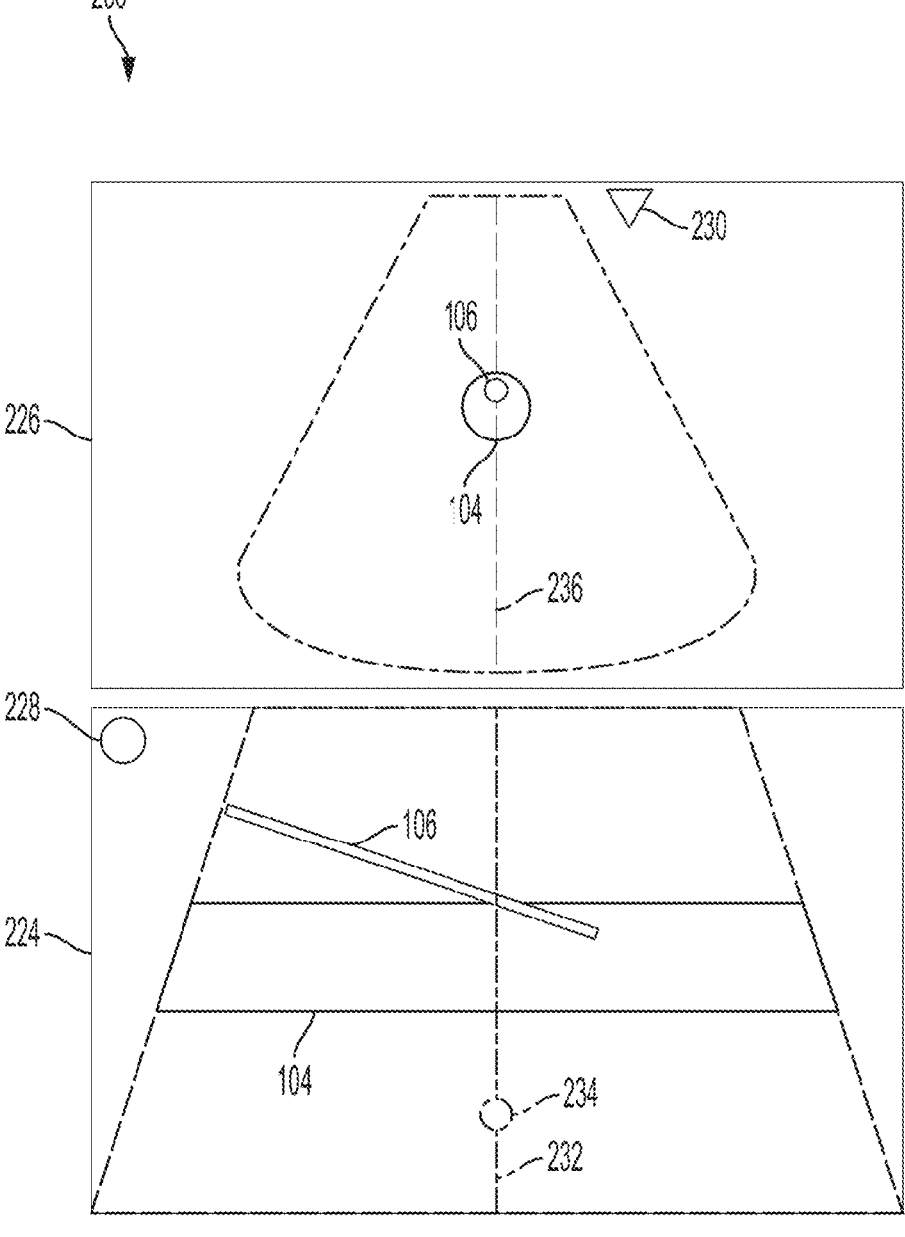
FIG. 2 illustrates an example graphical user interface (GUI) for biplane imaging, in accordance with certain embodiments described herein.

FIG. 2 illustrates an example graphical user interface (GUI) 200 for biplane imaging, in accordance with certain embodiments described herein. The GUI may be displayed by a processing device in operative communication with the ultrasound device 102. The GUI 200 includes a longitudinal ultrasound image 224, a transverse ultrasound image 226, a transverse imaging plane indicator 232, a longitudinal image orientation indicator 228, a longitudinal imaging plane indicator 236, and a transverse image orientation indicator 230. The transverse imaging plane indicator 232 includes a caliper 234. The transverse imaging plane indicator 232 and the longitudinal image orientation indicator 228 are superimposed on the longitudinal ultrasound image 224. The longitudinal imaging plane indicator 236 and the transverse image orientation indicator 230 are superimposed on the transverse ultrasound image 226.

The longitudinal ultrasound image 224 and the transverse ultrasound image 226 of FIG. 1 depict the vessel 104 and the needle 106 when the ultrasound device 102, the longitudinal imaging plane 112, the transverse imaging plane 114, the vessel 104, and the needle 106 are oriented as illustrated in FIG. 1. The longitudinal ultrasound image 224 is referred to as "longitudinal" because the ultrasound device that collected the longitudinal ultrasound image 224 is oriented such that a longitudinal view of the needle 106 is depicted by the longitudinal ultrasound image 224. The longitudinal ultrasound image 224 is collected with the longitudinal imaging plane 112, which is along the azimuthal dimension 108 of the ultrasound device 102. The transverse ultrasound image 226 is referred to as "transverse" because the ultrasound device 102 that collects the transverse ultrasound image 226 is oriented such that a transverse view of the needle 106 is depicted by the transverse ultrasound image 226. The transverse ultrasound image 226 is collected with the transverse imaging plane 114, which is along the elevational dimension 110 of the ultrasound device 102. Generally, however, the two ultrasound images in the GUI 200 may be collected by any two different imaging planes, and need not necessarily depict particular views of a needle, nor need they necessarily depict a needle at all. The processing device may update the GUI 200 with new longitudinal ultrasound images 224 and new transverse ultrasound images 226 in real-time as the ultrasound device collects new ultrasound images.

In some embodiments, the processing device may configure the ultrasound device 102 to alternate collection of longitudinal ultrasound images 224 and collection of transverse ultrasound images 226. In some embodiments, the ultrasound device 102 may include an ultrasound transducer array having a large number of ultrasound transducers arranged in a two-dimensional array. The ultrasound device 102 may collect the longitudinal ultrasound image 224 by transmitting and/or receiving ultrasound waves using an aperture (in other words, a subset of the ultrasound transducers) having a long dimension along the azimuthal dimension 108 of the ultrasound transducer array of the ultrasound device 102, such that the longitudinal imaging plane 112 is along the azimuthal dimension 108 of the ultrasound device 102. The ultrasound device 102 may collect the transverse ultrasound image 226 by transmitting and/or receiving ultrasound waves using an aperture having a long dimension along the elevational dimension 110 of the ultrasound transducer array of the ultrasound device 102, such that the transverse imaging plane 114 is along the elevational dimension 110 of the ultrasound device 102. Thus, alternating collection of the longitudinal ultrasound images 224 and collection of the transverse ultrasound images 226 may include alternating collection of ultrasound images using one aperture and collection of ultrasound images using another aperture. In some embodiments, the ultrasound device 102 may collect the longitudinal ultrasound images 224 and the transverse ultrasound images 226 using the same aperture but with different beamforming parameters used to generate the ultrasound images. Thus, alternating collection of the longitudinal ultrasound images 224 and collection of the transverse ultrasound images 226 may include alternating generation of ultrasound images using one set of beamforming parameters and generation of ultrasound images using another set of beamforming parameters. It should be appreciated that the ultrasound device 102 may collect both types of ultrasound images without the operator needing to rotate the ultrasound device 102. The ultrasound device 102 may use its ability to change the aperture and/or change beamforming parameters in order to collect ultrasound images with different imaging planes without the operator needing to rotate the ultrasound device 102.

In some embodiments, alternating collection of the ultrasound images may be at a rate in the range of approximately 15-30 Hz. In some embodiments, the ultrasound device 102 may be configured to collect one ultrasound image with the longitudinal imaging plane 112, then collect one ultrasound image with the transverse imaging plane 114, then collect one ultrasound image with the longitudinal imaging plane 112, etc. In some embodiments, the ultrasound device 102 may be configured to collect one or more ultrasound images with longitudinal imaging plane 112, then collect one or more ultrasound images with the transverse imaging plane 114, then collect one or more ultrasound images with the longitudinal imaging plane 112, etc.

The transverse imaging plane indicator 232 may indicate the location of the transverse imaging plane 114. In particular, the transverse imaging plane indicator 232 may indicate where the transverse imaging plane 114 intersects with longitudinal imaging plane 112. Every location in the longitudinal ultrasound image 224 may correspond to a location in the real world (e.g., within a subject), and the transverse imaging plane 114 may intersect the longitudinal imaging plane 112 at a location in the real world corresponding to the location of the transverse imaging plane indicator 232 in the longitudinal ultrasound image 224.

The longitudinal imaging plane indicator 236 may indicate the location of the longitudinal imaging plane 112. In particular, the longitudinal imaging plane indicator 236 may indicate where the longitudinal imaging plane 112 intersects with the transverse imaging plane 114. In particular, every location in the transverse ultrasound image 226 may correspond to a location in the real world (e.g., within a subject), and the longitudinal imaging plane 112 may intersect the transverse imaging plane 114 at a location in the real world corresponding to the location of the longitudinal imaging plane indicator 236 in the transverse ultrasound image 226. In some embodiments, if the transverse imaging plane 114 and the longitudinal imaging plane 112 are orthogonal to each other, the transverse imaging plane indicator 232 and the longitudinal imaging plane indicator 236 may be straight vertical lines through the longitudinal ultrasound image 224 and the transverse ultrasound image 226, respectively (as in FIG. 2).

Figure 3:
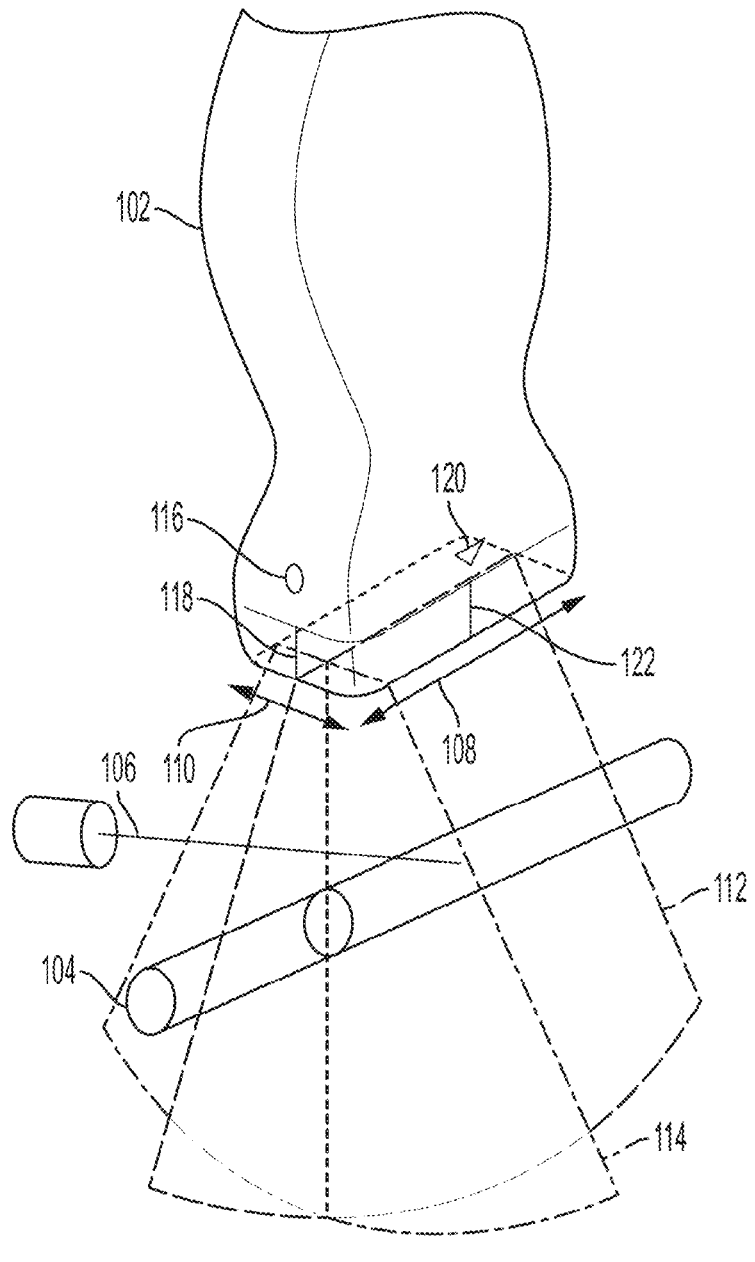
FIG. 3 illustrates a schematic diagram of another example of an ultrasound device imaging a needle being inserted into a subject, in accordance with certain embodiments described herein.

In FIG. 1, the transverse imaging plane 114 intersects the vessel 104 at a location where the tip of the needle 106 is inside the vessel 104. Therefore, in the transverse ultrasound image 226 in FIG. 2, the needle 106 is inside the vessel 104. FIG. 3 illustrates a schematic diagram of another example of an ultrasound device 102 imaging a needle 106 being inserted into a vessel 104, in accordance with certain embodiments described herein. In FIG. 3, the transverse imaging plane 114 is in a different location than in FIG. 1.

Figure 4:
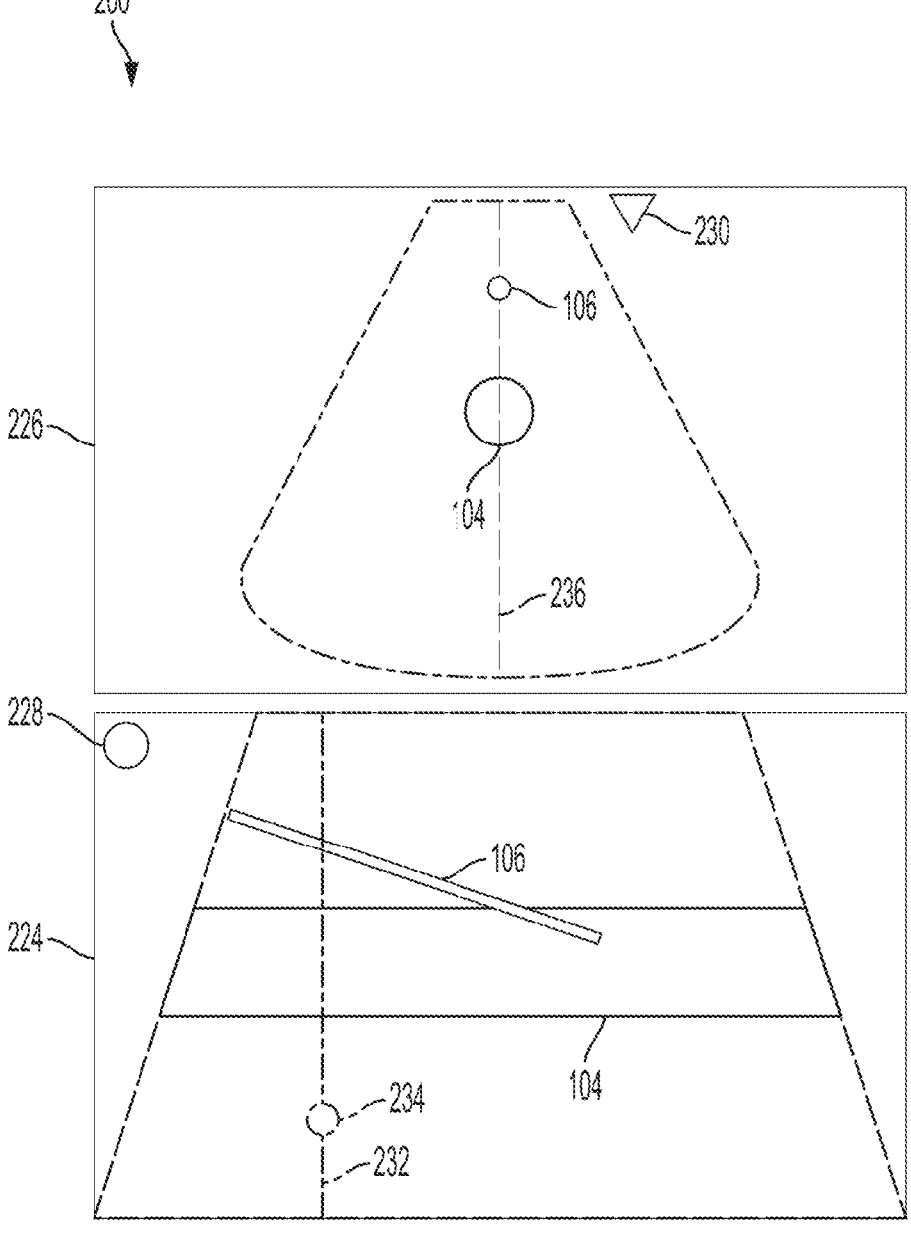
FIG. 4 illustrates another example of the GUI of FIG. 2, in accordance with certain embodiments described herein.

Referring back to FIG. 2, in some embodiments, the GUI 200 may enable a user to cause the processing device to configure the ultrasound device to modify the location of the transverse imaging plane 114. In some embodiments, a user may drag the caliper 234 on the transverse imaging plane indicator 232 to a new selected location (e.g., by touching and dragging or clicking and dragging) on the longitudinal ultrasound image 224. In some embodiments, in response to detecting this dragging movement, if the dragging movement covers a particular distance left or right across the longitudinal ultrasound image 224, the processing device may move the transverse imaging plane indicator 232 left or right by that distance to a new location on the longitudinal ultrasound image 224. Furthermore, the processing device may configure the ultrasound device 102 to modify the location of the transverse imaging plane 114 based on the new selected location. In particular, the processing device may configure the ultrasound device 102 to modify the location of the transverse imaging plane 114 such that the transverse imaging plane 114 intersects the longitudinal imaging plane 112 at a location in the real world corresponding to the location of the transverse imaging plane indicator 232 in the longitudinal ultrasound image 224. In some embodiments, the caliper 234 may not be displayed, and the processing device may move the transverse imaging plane indicator 232 and configure the ultrasound device 102 to modify the location of the transverse imaging plane 114 based on a dragging movement beginning anywhere on the transverse imaging plane indicator 232. In some embodiments, in response to detecting a selection of a location on the longitudinal ultrasound image 224 (e.g., by touching or clicking a location, without dragging), the processing may move the transverse imaging plane indicator 232 to the selected location and configure the ultrasound device 102 to modify the location of the transverse imaging plane 114 based on the selected location. FIG. 4 illustrates another example of the GUI 200, in accordance with certain embodiments described herein. The longitudinal ultrasound image 224 and the transverse ultrasound image 226 of FIG. 4 depict the vessel 104 and the needle 106 when the ultrasound device 102, the longitudinal imaging plane 112, the transverse imaging plane 114, the vessel 104, and the needle 106 are oriented as illustrated in FIG. 3. The transverse imaging plane indicator 232 in FIG. 4 is at a different location than the location in FIG. 2. The processing device may have moved the transverse imaging plane indicator 232 to the new location based on a user selection. Additionally, the processing device may have configured the ultrasound device 102 to modify the location of the transverse imaging plane 114 based on the user selection of the new location. In FIG. 3, the transverse imaging plane 114 intersects the vessel 104 at a location where the tip of the needle 106 is above the vessel 104. Therefore, in the transverse ultrasound image 226 in FIG. 4, the needle 106 is above the vessel 104.

In the example of FIGS. 2 and 4, the processing device does enable a user to modify the location of the transverse imaging plane 114 but does not enable the user to modify the location of the longitudinal imaging plane 112. Therefore, the longitudinal imaging plane indicator 236 is displayed with a different format than the transverse imaging plane indicator 232, namely, dashed versus straight line, although other changes in format such as color may be used. In some embodiments, the processing device may enable a user to modify the location of the longitudinal imaging plane 112. In such embodiments, the longitudinal imaging plane indicator 236 may be displayed with the same format as the transverse imaging plane indicator 232. The transverse imaging plane indicator 232 may include a caliper like the caliper 234, and the processing device may move the longitudinal imaging plane indicator 236 and configure the ultrasound device 102 to modify the location of the longitudinal imaging plane 112 based on a user selection in the same manner as described above for the transverse imaging plane 114.

The transverse imaging plane indicator 232 and/or the longitudinal imaging plane indicator 236 may help a user to visualize and understand the locations of the transverse imaging plane 224 and/or the longitudinal imaging plane 112, and this may help to reduce user confusion in performing biplane imaging.

In some embodiments, to configure the ultrasound device to modify the location of an imaging plane, the processing device may configure the ultrasound device 102 to move the aperture (in other words, a subset of the ultrasound transducers) used for transmitting and/or receiving ultrasound waves. For example, if the aperture has a long dimension extending across the elevational dimension 110 of the ultrasound transducer array of the ultrasound device 102 and the center of the short dimension of the aperture is at a particular location on the azimuthal dimension 108, the processing device may configure the ultrasound device 102 to translate the aperture such that the center of the short dimension of the aperture is at a different location on the azimuthal dimension 108. In some embodiments, to configure the ultrasound device to modify the location of an imaging plane, the processing device may configure the ultrasound device to steer the imaging plane. For example, if the aperture is along the elevational dimension 110 of the ultrasound transducer array, the processing device may steer the imaging plane to a different azimuthal angle. In some embodiments, for shallower imaging depths (e.g., less than a threshold depth), to move an imaging plane, the processing device may configure the ultrasound device to translate the aperture. For deeper imaging depths (e.g., greater than a threshold depth), to move an imaging plane, the processing device may configure the ultrasound device 102 to steer the imaging plane at an angle. In any case, the processing device may configure the ultrasound device to modify the location of the imaging plane such that the new position of the imaging plane corresponds to the location in the ultrasound image selected by the user, which may be the same as the new location of the corresponding imaging plane indicator. It should be appreciated that the ultrasound device 102 may collect both types of ultrasound images without the operator needing to move the ultrasound device 102. The ultrasound device 102 may use its ability to change the aperture and/or change beamforming parameters in order to modify the location of imaging planes without the operator needing to move the ultrasound device 102.

Figure 5:
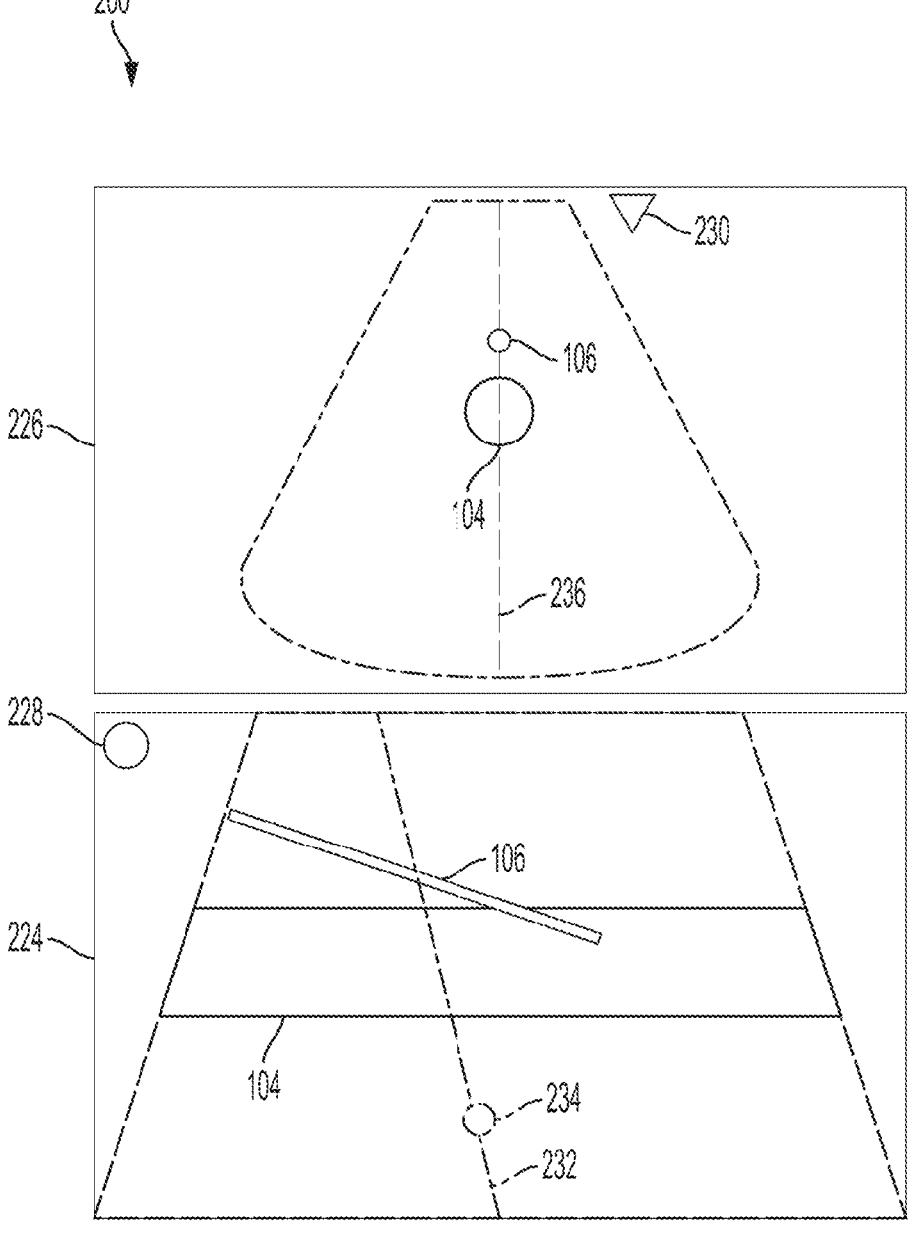
FIG. 5 illustrates another example of the GUI of FIG. 2, in accordance with certain embodiments described herein.

In some embodiments, if the transverse imaging plane 114 and the longitudinal imaging plane 112 are not orthogonal to each other (e.g., one or both of the imaging planes have been steered at angles), one or both of the transverse imaging plane indicator 232 and the longitudinal imaging plane indicator 236 may be diagonal vertical lines through the longitudinal ultrasound image 224 and the transverse ultrasound image 226, respectively. FIG. 5 illustrates another example of the GUI 200, in accordance with certain embodiments described herein. The transverse imaging plane indicator 232 is a diagonal line. The transverse imaging plane indicator 232 may be a diagonal line because the transverse imaging plane 114 has been steered at an azimuthal angle. The processing device may have moved the transverse imaging plane indicator 232 to the new location and orientation based on a user selection. Additionally, the processing device may have configured the ultrasound device 102 to modify the location and/or orientation of the transverse imaging plane 114 based on the user selection.

In FIGS. 2 and 4-5, the longitudinal image orientation indicator 228 is superimposed on the left of the longitudinal ultrasound image 224. The longitudinal image orientation indicator 228 may indicate the orientation of the longitudinal ultrasound image 224 relative to the marker 116. For example, because the longitudinal image orientation indicator 228 is on the left side of the longitudinal ultrasound image 224, this may indicate that portions on the left of the longitudinal ultrasound image 224 depict portions of the vessel 104 and needle 106 below the side of the ultrasound device that has the marker 116. The transverse image orientation indicator 230 may indicate the orientation of the transverse ultrasound image 226 relative to the marker 120. For example, because the transverse image orientation indicator 230 is on the right side of the transverse ultrasound image 226, this may indicate that portions on the right of the transverse ultrasound image 226 depict portions of the vessel 104 and needle 106 below the side of the ultrasound device that has the marker 120. Generally, the longitudinal image orientation indicator 228 may be displayed on either the right or left side of the longitudinal ultrasound image 224, and the transverse image orientation indicator 230 may be displayed on either the right or left side of the transverse ultrasound image 226. Whether the orientation indicators are displayed on the right or left side may be user-controllable. In some embodiments, only the longitudinal image orientation indicator 228 may be displayed, or only the transverse image orientation indicator 230 may be displayed, or neither may be displayed.

Figure 6:
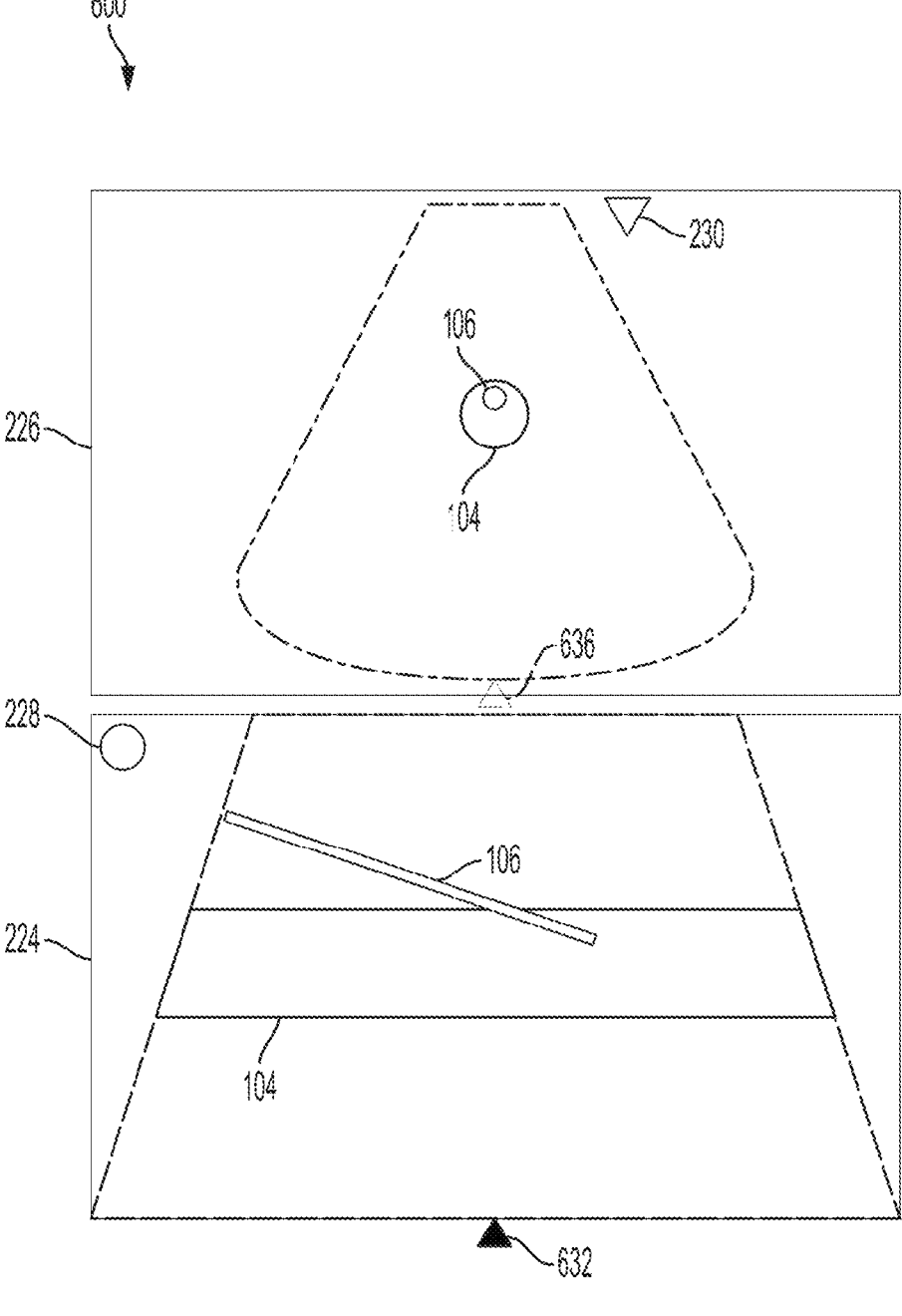
FIG. 6 illustrates another example GUI for biplane imaging, in accordance with certain embodiments described herein.

FIG. 6 illustrates another example GUI 600 for biplane imaging, in accordance with certain embodiments described herein. The GUI 600 is the same as the GUI 200, except that the GUI 600 includes the transverse imaging plane indicator 632 instead of the transverse imaging plane indicator 232, and the GUI 600 includes the longitudinal imaging plane indicator 636 instead of the longitudinal imaging plane indicator 236. In contrast to the transverse imaging plane indicator 232 and the longitudinal imaging plane indicator 236, which are lines extending through ultrasound images, the transverse imaging plane indicator 632 and the longitudinal imaging plane indicator 636 are markers at edges of the ultrasound images. The transverse imaging plane indicator 632 and the longitudinal imaging plane indicator 636 may generally indicate the positions of the transverse imaging plane 114 and the longitudinal imaging plane 112, respectively. For example, if the imaging planes are orthogonal to each other, the imaging plane indicators may indicate that the imaging planes are located at positions in the real world corresponding to locations in the ultrasound images extending from the imaging plane indicators vertically to the top of the ultrasound images. If the imaging planes are at angles to each other, the imaging plane indicators may indicate that the imaging planes are located at positions in the real world corresponding to locations in the ultrasound images extending from the imaging plane indicators diagonally to the top of the ultrasound images.

Figure 7:
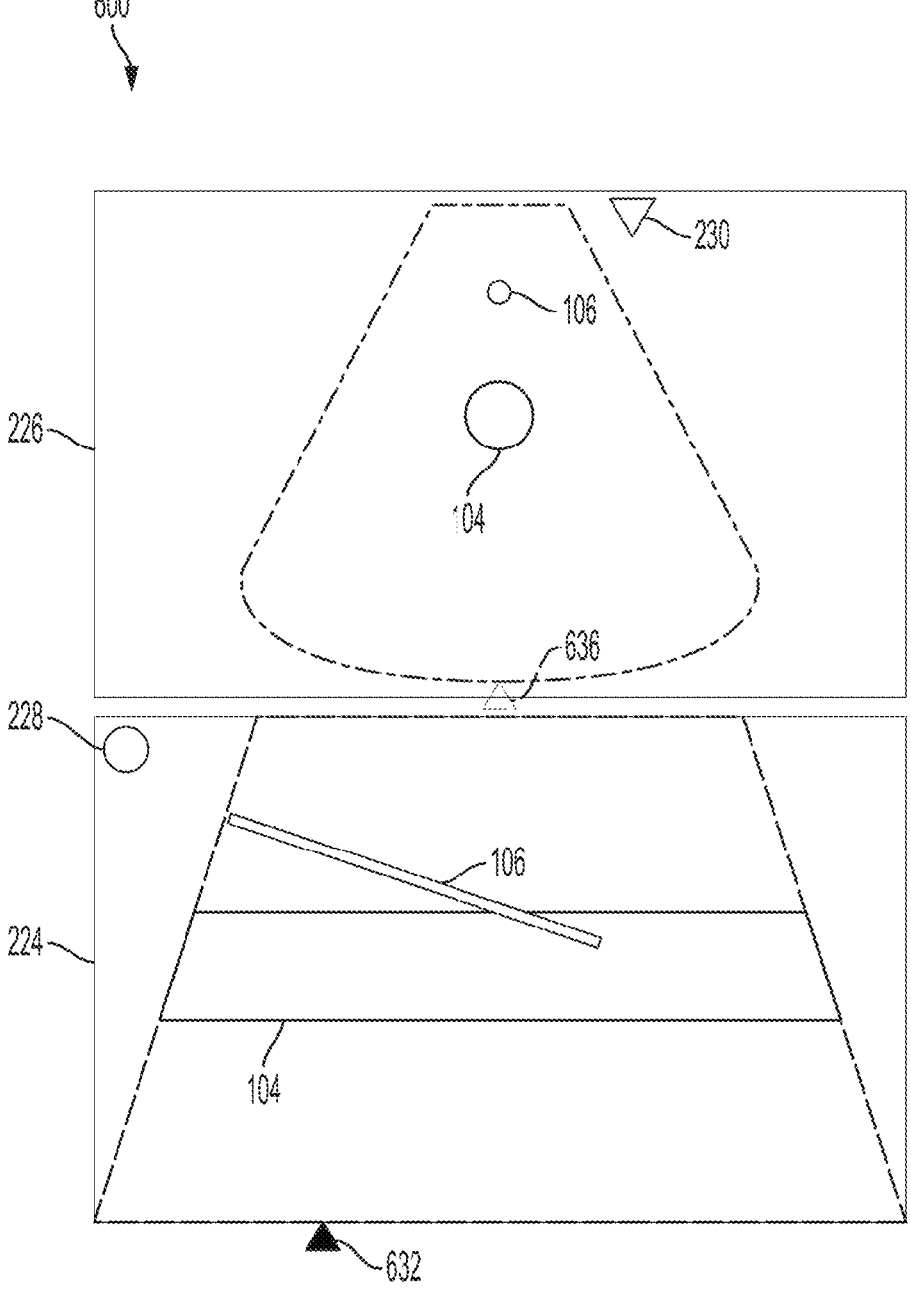
FIG. 7 illustrates another example of the GUI of FIG. 6, in accordance with certain embodiments described herein.

The processing device may move one or both of the imaging plane indicators of FIG. 6 based on a user selection, and configure the ultrasound device 102 to move the imaging planes based on the user selection. In some embodiments, a user may drag the transverse imaging plane indicator 632 to a new selected location (e.g., by touching and dragging or clicking and dragging) on the edge of the longitudinal ultrasound image 224. In some embodiments, in response to detecting this dragging movement, if the dragging movement covers a particular distance left or right along the edge of the longitudinal ultrasound image 224, the processing device may move the transverse imaging plane indicator 232 left or right by that distance to a new location on the edge of the longitudinal ultrasound image 224. Furthermore, the processing device may configure the ultrasound device 102 to modify the location of the transverse imaging plane 114 based on the new selected location. In particular, the processing device may configure the ultrasound device 102 to modify the location of the transverse imaging plane such that the transverse imaging plane 114 intersects the longitudinal imaging plane 112 at a location in the real world corresponding to the location of the transverse imaging plane indicator 232 in the longitudinal ultrasound image 224. In some embodiments, in response to detecting a selection of a location on the edge of the longitudinal ultrasound image 224 (e.g., by touching or clicking a location, without dragging), the processing may move the transverse imaging plane indicator 232 to the selected location and configure the ultrasound device to modify the location of the transverse imaging plane 114 based on the selected location. FIG. 7 illustrates another example of the GUI 600, in accordance with certain embodiments described herein. The transverse imaging plane indicator 632 in FIG. 7 is at a different location than the location in FIG. 6. The processing device may have moved the transverse imaging plane indicator 904 to the new location based on a user selection. Additionally, the processing device may have configured the ultrasound device 102 to modify the location of the transverse imaging plane 114 based on the user selection.

In the example of FIGS. 6-7, the processing device does enable a user to modify the location of the transverse imaging plane 114 but does not enable the user to modify the location of the longitudinal imaging plane 112. Therefore, the longitudinal imaging plane indicator 636 is displayed with a different format than the transverse imaging plane indicator 632, namely, empty versus filled, although other changes in format such as color may be used. In some embodiments, the processing device may enable a user to modify the location of the longitudinal imaging plane 112. In such embodiments, the longitudinal imaging plane indicator 636 may be displayed with the same format as the transverse imaging plane indicator 632. The processing device may move the longitudinal imaging plane indicator 636 and configure the ultrasound device 102 to modify the location of the longitudinal imaging plane 112 based on a user selection in the same manner as described above for the transverse imaging plane 114.

Figure 8:
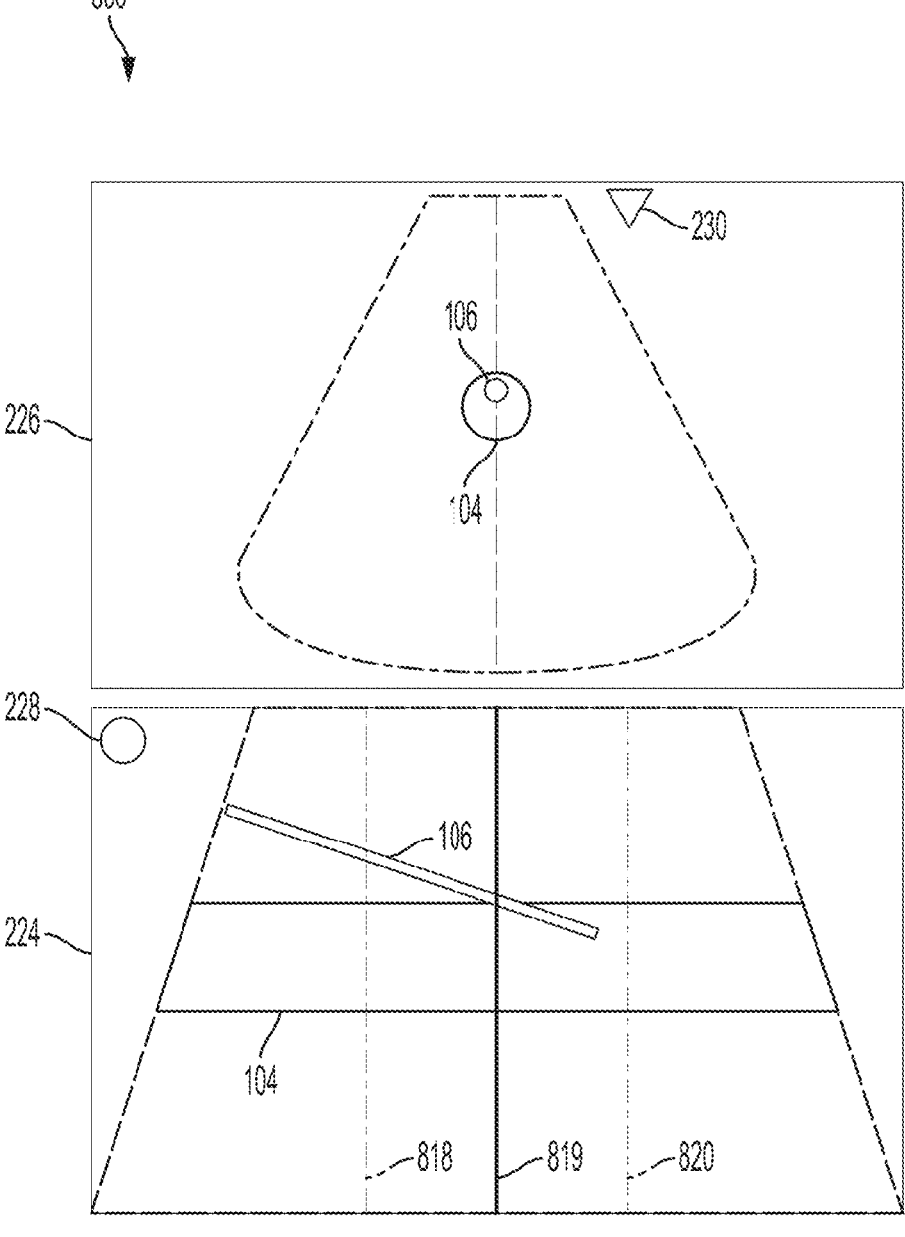
FIG. 8 illustrates another example GUI for biplane imaging, in accordance with certain embodiments described herein.

FIG. 8 illustrates another example GUI 800 for biplane imaging, in accordance with certain embodiments described herein. The GUI 800 is the same as the GUI 200, except that the GUI 800 includes the transverse imaging plane options 818, 819, and 820 instead of the transverse imaging plane indicator 232. In some embodiments, in response to receiving a selection from a user of one of the transverse imaging plane options 818-820 (e.g., by touching or clicking), the processing device may configure the ultrasound device 102 to modify the location of the transverse imaging plane 114 such that the new position of the transverse imaging plane 114 corresponds to the selected transverse imaging plane option. Additionally, the processing device may highlight the selected transverse imaging plane option in the GUI 800. Thus, in FIG. 8, the transverse imaging plane option 819 is highlighted (i.e., is in solid rather than dashed), indicating that the location of the transverse imaging plane 114 corresponds to the location of the transverse imaging plane option 819 in the longitudinal ultrasound image 224. In contrast to the GUI 200, which may allow for the user to select any location on the longitudinal ultrasound image 224 for moving the transverse imaging plane 114, the GUI 800 may only allow for three locations of the transverse imaging plane 114. It should be appreciated that there may be other numbers of options, such as two or more than three. In some cases, allowing for fewer options may be a helpful simplification in the GUI 800 and/or the technology implementing the biplane imaging.

Figure 9A:
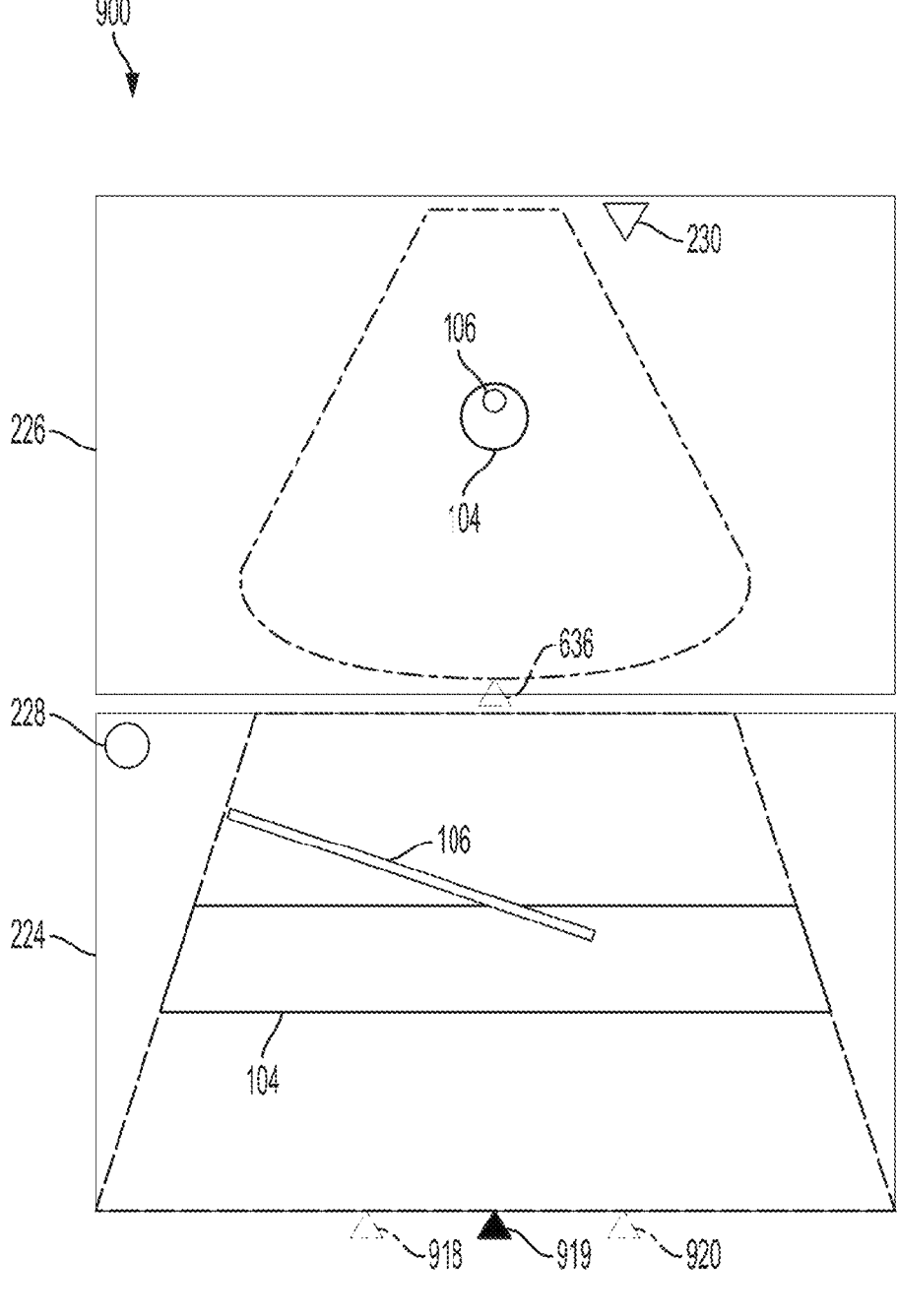
FIG. 9A illustrates another example GUI for biplane imaging, in accordance with certain embodiments described herein.

FIG. 9A illustrates another example GUI 900 for biplane imaging, in accordance with certain embodiments described herein. The GUI 900 is the same as the GUI 600, except that the GUI 900 includes the transverse imaging plane options 918, 919, and 920 instead of the transverse imaging plane indicator 632. In some embodiments, in response to receiving a selection from a user of one of the transverse imaging plane options 918-920 (e.g., by touching or clicking), the processing device may configure the ultrasound device 102 to modify the location of the transverse imaging plane 114 such that the new position of the transverse imaging plane 114 corresponds to selection transverse imaging plane option. Additionally, the processing device may highlight the selected transverse imaging plane option in the GUI 900. Thus, in FIG. 9A, the transverse imaging plane option 919 is highlighted (i.e., filled rather than empty), indicating that the location of the transverse imaging plane 114 corresponds to the location of the transverse imaging plane option 919 relative to the longitudinal ultrasound image 224. Thus, in contrast to the GUI 600, which may allow for the user to select any location on the longitudinal ultrasound image 224 for moving the transverse imaging plane 114, the GUI 900 may only allow for three locations of the transverse imaging plane 114. It should be appreciated that there may be other numbers of options, such as two or more than three. In some cases, allowing for fewer options may be a helpful simplification in the GUI 900 and/or the technology implementing the biplane imaging.

Figure 9C:
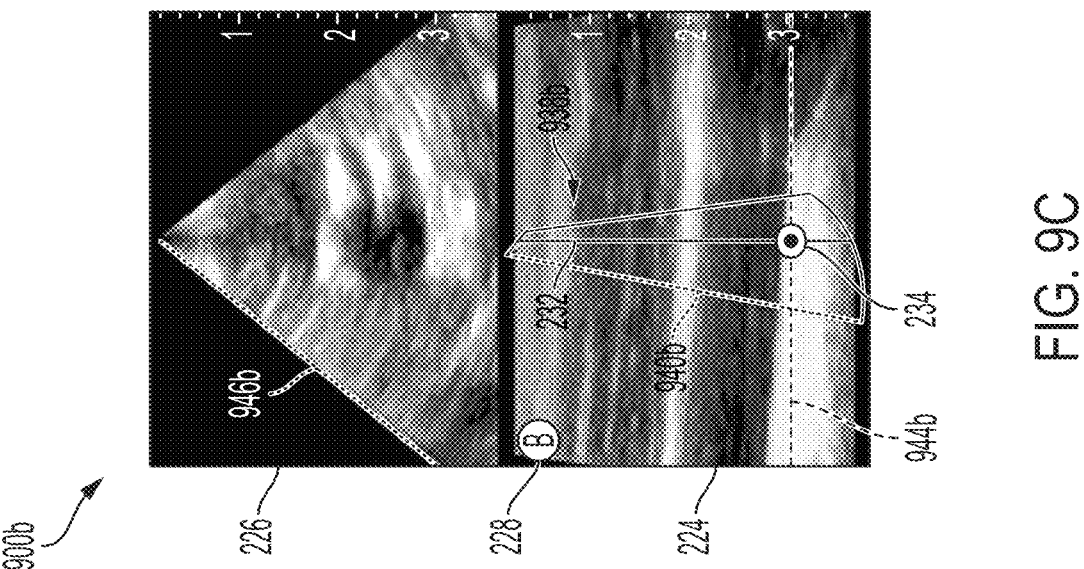
FIG. 9C illustrates another example of the GUI of FIG. 9B, in accordance with certain embodiments described herein.
Figure 9B:
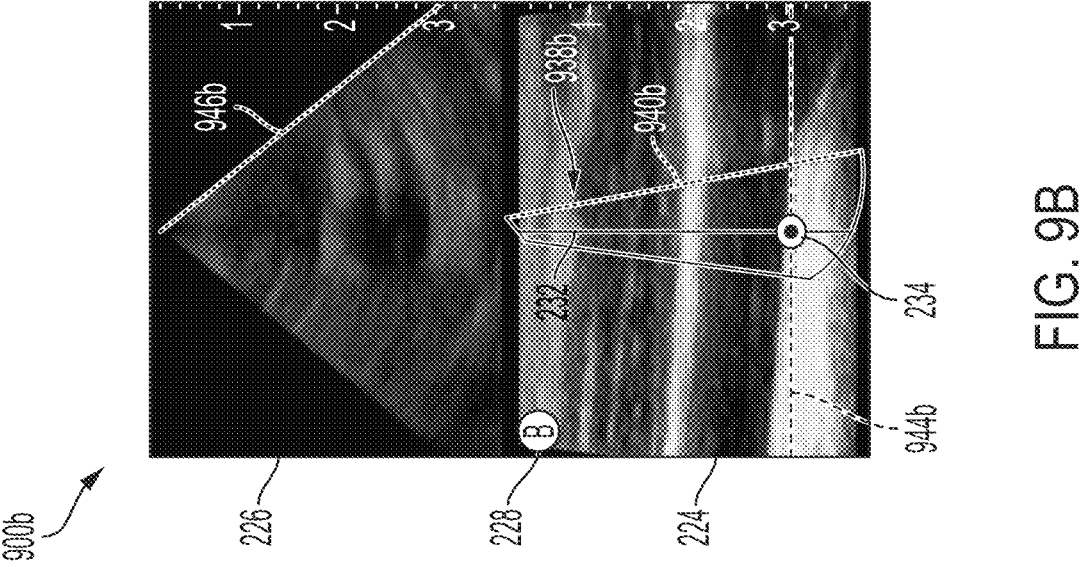
FIG. 9B illustrates another example GUI for biplane imaging, in accordance with certain embodiments described herein.

FIG. 9B illustrates another example GUI 900*b* for biplane imaging, in accordance with certain embodiments described herein. The GUI 900*b* includes the longitudinal ultrasound image 224, the transverse ultrasound image 226, the transverse imaging plane indicator 232, the caliper 234, the longitudinal image orientation indicator 228, a transverse imaging plane visualization 938*b*, and a freedom-of-movement indicator 944*b*. The transverse imaging plane visualization 938*b* includes a highlighted edge 940*b*. The transverse ultrasound image 226 includes a highlighted edge 946*b*. The freedom-of-movement indicator 944*b* may depict the freedom of movement for the transverse imaging plane indicator 232. In other words, the freedom-of-movement indicator 944*b* may indicate the range of possible positions for the transverse imaging plane indicator 232 (and in particular, the caliper 234 on the transverse imaging plane indicator 232). In some embodiments, the freedom-of-movement indicator 944*b* may be absent.

The transverse imaging plane visualization 938*b* may be a three-dimensional visualization of the location of the transverse imaging plane 114. The transverse imaging plane visualization 938*b* thus may illustrate a slice through the longitudinal ultrasound image 224, where the slice represents the transverse imaging plane 114. The location of the highlighted edge 940*b* of the transverse imaging plane visualization 938*b* corresponds to the highlighted edge 946*b* of the transverse ultrasound image 226. In other words, regions depicted adjacent to the highlighted edge 946*b* of the transverse ultrasound image 226 were collected from regions of the transverse imaging plane 114 depicted adjacent to the highlighted edge 940*b* of the transverse imaging plane visualization 938*b*. Thus, the highlighted edge 940*b* and the highlighted edge 946*b* may serve as indicators for the orientation of the transverse ultrasound image 226 relative to the transverse imaging plane 114.

FIG. 9C illustrates another example of the GUI 900*b*, in accordance with certain embodiments described herein. In FIG. 9C, the highlighted edge 940*b* of the transverse imaging plane visualization 938*b* is on the left side, whereas in FIG. 9B it is on the right side. Additionally, in FIG. 9C, the highlighted edge 946*b* of the transverse ultrasound image 226 is on the left side, whereas in FIG. 9B it is on the right side. Thus, FIG. 9C illustrates a different orientation of the transverse ultrasound image 226 relative to the transverse imaging plane 114. In some embodiments, upon receiving a selection (e.g., a tap or a click) from the user of the highlighted edge 946*b*, the processing device may switch the orientation of the transverse ultrasound image 226 relative to the transverse imaging plane 114. In other words, if the orientation was as in FIG. 9B, the processing device may switch the orientation to that of FIG. 9C, and vice versa.

In some embodiments, the transverse imaging plane visualization 938*b* may appear in the GUI 900*b* when a user interacts with (e.g., touches or hovers over) the highlighted edge 946*b* of the transverse ultrasound image 226, the transverse imaging plane indicator 232, and/or the caliper 234. In such embodiments, the transverse imaging plane visualization 938*b* may appear, persist for a period of time, and then disappear.

Figure 9D:
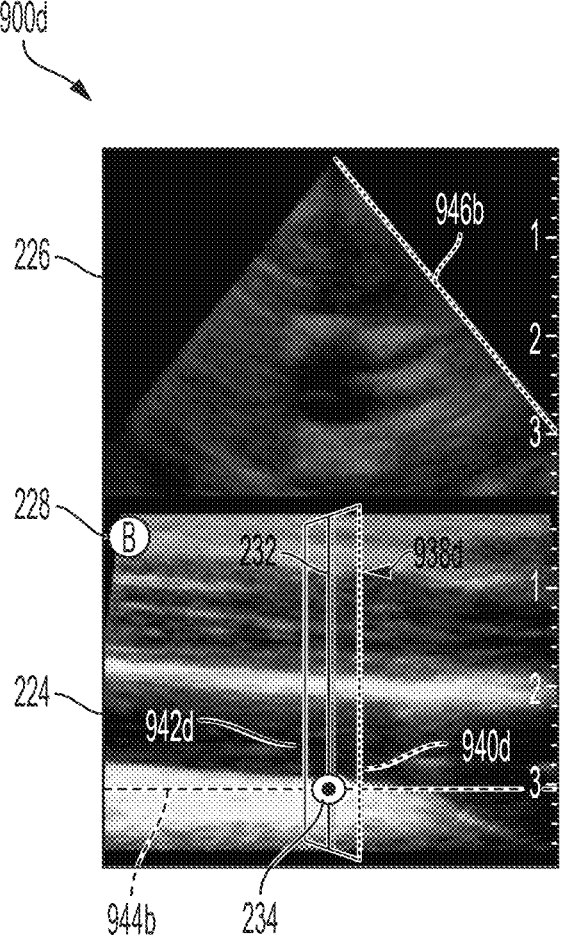
FIG. 9D illustrates another example GUI for biplane imaging, in accordance with certain embodiments described herein.

FIG. 9D illustrates another example GUI 900*d* for biplane imaging, in accordance with certain embodiments described herein. The GUI 900*d* includes the longitudinal ultrasound image 224, the transverse ultrasound image 226, the transverse imaging plane indicator 232, the caliper 234, the longitudinal image orientation indicator 228, a transverse imaging plane visualization 938*d*, and a freedom-of-movement indicator 944*b*. The transverse imaging plane visualization 938*d* includes a highlighted edge 940*d*. The transverse ultrasound image 226 includes the highlighted edge 946*b*. The transverse imaging plane visualization 938*d* and its highlighted edge 940*d* are the same as the transverse imaging plane visualization 938*b* and its highlighted edge 940*b*, except that the transverse imaging plane visualization 938*b* has a square-like shape whereas the transverse imaging plane visualization 938*b* has a sector-like shape.

It should be appreciated that the transverse imaging plane visualization 938*b*, the transverse imaging plane visualization 938*d*, the highlighted edge 946*b* of the transverse ultrasound image 226, and/or the freedom-of-movement indicator 944*b* may be added to any of the other GUIs (e.g., the GUIs 200, 600, 800, or 900) described herein. It should also be appreciated that any aspects of the other GUIs (e.g., the GUIs 200, 600, 800, or 900) described herein may be added to the GUIs 900*b* and/or 900*d* or substituted for aspects of the GUIs 900*b* and/or 900*d*. For example, the transverse imaging plane options 818-820 or 918-920 may be substituted for the transverse imaging plane indicator 232. As another example, the longitudinal imaging plane indicator 236, the longitudinal imaging plane indicator 636, and/or the transverse image orientation indicator 230 may be added to the GUIs 900*b* and/or 900*d*.

FIG. 10 illustrates a process 1000 for biplane imaging, in accordance with certain embodiments described herein. The process 1000 is performed by a processing device in operative communication with an ultrasound device (e.g., the ultrasound device 102). For example, the processing device may be a mobile phone, tablet, or laptop. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link). The process 1000 is generally directed to receiving a user selection to modify a position of an ultrasound imaging plane and configuring the ultrasound device to modify the position of the ultrasound imaging plane based on the user selection.

In act 1002, the processing device configures the ultrasound device to alternate collection of ultrasound images with an imaging plane (e.g., the imaging plane 112) along the azimuthal dimension (e.g., the azimuthal dimension 108) of the ultrasound device (or more specifically, of the ultrasound transducer array of the ultrasound device) and ultrasound images with an imaging plane (e.g., the imaging plane 114) along the elevational dimension (e.g., the elevational dimension 110) of the ultrasound device. The ultrasound image with the imaging plane along the azimuthal dimension of the ultrasound may be the longitudinal ultrasound image 224 and the ultrasound image with the imaging plane along the elevational dimension of the ultrasound device may be the transverse ultrasound image 226. Further description of collecting ultrasound images with different imaging planes may be found with reference to FIGS. 1-9D. In some embodiments, alternating collection of the ultrasound images may be at a rate in the range of approximately 15-30 Hz. In other words, the time period between collection of each successive ultrasound image, where successive ultrasound images may have different imaging planes, may be in the range of approximately ⅟30-⅟15 seconds. In some embodiments, the ultrasound device may be configured to collect one ultrasound image with the imaging plane along the azimuthal dimension, then collect one ultrasound image with the imaging plane along the elevational dimension, then collect one ultrasound image with the imaging plane along the azimuthal dimension, etc. In some embodiments, the ultrasound device may be configured to collect one or more ultrasound images with the imaging plane along the azimuthal dimension, then collect one or more ultrasound images with the imaging plane along the elevational dimension, then collect one or more ultrasound images with the imaging plane along the azimuthal dimension, etc. In some embodiments, the processing device may transmit commands to the ultrasound device to configure the ultrasound device to alternate collection of the ultrasound images. In some embodiments, however, the ultrasound device may be already be configured to alternate collection of the ultrasound images, such that act 1002 may be omitted. The process 1000 proceeds from act 1002 to act 1004.

In act 1004, the processing device simultaneously displays one of the ultrasound images with the imaging plane along the azimuthal dimension of the ultrasound device and one of the ultrasound images with the imaging plane along the elevational dimension of the ultrasound device. In some embodiments, the processing device may update the display as new ultrasound images are collected. In some embodiments, the processing device may display the ultrasound images on its own display screen. In some embodiments, the processing device may generate the ultrasound images for display on a display screen of another device. In some embodiments, the display screen may display the ultrasound images one of top of another. In some embodiments, the display screen may display the ultrasound images horizontally next to each other. Further description of displaying ultrasound images may be found with reference to FIGS. 2 and 4-9D. The process 1000 proceeds from act 1004 to act 1006.

In act 1006, the processing device receives a user selection to modify a position of the imaging plane along the azimuthal dimension of the ultrasound device and/or a position of the imaging plane along the elevational dimension of the ultrasound device. In some embodiments, the processing device receives the user selection through a GUI displayed by the processing device. In some embodiments, the GUI includes an indicator of the position of the imaging plane (e.g., the transverse imaging plane indicator 232 and/or the longitudinal imaging plane indicator 236). Further description of receiving a user selection through a GUI to modify a position of an imaging plane may be found with reference to FIGS. 2 and 4-9D.

In some embodiments, instead of or in addition to the processing device receiving a selection from a GUI to modify the location of the imaging plane, the processing device may receive a selection to modify the location of the imaging plane based on the processing device detecting a tilt of the processing device and/or based on the ultrasound device detecting a tilt of the ultrasound device. The processing device and/or the ultrasound device may detect a tilt using a motion sensor (e.g., including an accelerometer, gyroscope, and/or magnetometer). In embodiments including detection of a tilt of the ultrasound device, the ultrasound device may transmit an indication of the tilt to the processing device.

In some embodiments, instead of or in addition to the processing device receiving a selection from a GUI to modify the location of the imaging plane, the processing device may receive a selection to modify the location of the imaging plane based on the processing device detecting one or more taps on the exterior of the ultrasound device. The ultrasound device may detect taps using tap detection circuitry, which may include a motion sensor (e.g., including an accelerometer, gyroscope, and/or magnetometer). In some embodiments, the ultrasound device may transmit an indication of the detection of the one or more taps to the processing device, which may then transmit a command to the ultrasound device to change the location of an imaging plane.

In some embodiments, instead of or in addition to the processing device receiving a selection from a GUI to modify the location of the imaging plane, the processing device may receive a selection to modify the location of the imaging plane based on the processing device receiving a voice command from a user. The processing device may receive a voice command through a speaker on the processing device.

In some embodiments, the processing device may receive the user selection to modify the location of the imaging plane without receiving a user selection to change an ultrasound imaging mode or an ultrasound imaging preset (i.e., a set of parameters optimized for imaging a particular anatomical structure or region.) The process 1000 proceeds from act 1006 to act 1008.

In act 1008, the processing device configures the ultrasound device to modify the position of the imaging plane along the azimuthal dimension of the ultrasound device and/or the position of the imaging plane along the elevational dimension of the ultrasound device based on the user selection. Further description of configuring the ultrasound device to modify the position of an imaging plane based on a user selection may be found with reference to FIGS. 2 and 4-9D. It should be appreciated that while the process 1000 describes imaging planes along the azimuthal and elevational dimensions of the ultrasound device, the same process may also be applied to other imaging planes.

In some embodiments, acts 1002 and/or 1004 may be absent. For example, the ultrasound device may collect ultrasound images having just one imaging plane, the processing device may receive a user selection to modify the position of the imaging plane, and the processing device may configure the ultrasound device to modify the position of the imaging plane based on the user selection. As another example, in some embodiments, the ultrasound device may collect ultrasound images with two imaging planes but not simultaneously display the ultrasound images.

FIG. 11 illustrates another process 1100 for biplane imaging, in accordance with certain embodiments described herein. The process 1100 is performed by a processing device in operative communication with an ultrasound device (e.g., the ultrasound device 102). For example, the processing device may be a mobile phone, tablet, or laptop. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link). The process 1100 is generally directed to receiving a user selection to modify a position of an ultrasound imaging plane and configuring the ultrasound device to modify the position of the ultrasound imaging plane based on the user selection.

In act 1102, the processing device configures the ultrasound device to alternate collection of ultrasound images (e.g., the longitudinal ultrasound image 224) depicting a longitudinal view of an object (e.g., a needle such as the needle 106) and ultrasound images (e.g., the transverse ultrasound image 226) depicting a transverse view of the object. In some embodiments, the ultrasound image depicting the longitudinal view of the object may be collected with an imaging plane (e.g., the imaging plane 112) along the azimuthal dimension (e.g., the azimuthal dimension 108) of the ultrasound device (or more specifically, of the ultrasound transducer array of the ultrasound device) and the ultrasound image depicting the transverse view of the object may be collected with an imaging plane (e.g., the imaging plane 114) along the elevational dimension (e.g., the elevational dimension 110) of the ultrasound device. Further description of collecting ultrasound images with different imaging planes may be found with reference to FIGS. 1-9D. In some embodiments, the processing device may transmit commands to the ultrasound device to configure the ultrasound device to alternate collection of the ultrasound images. In some embodiments, however, the ultrasound device may be already be configured to alternate collection of the ultrasound images, such that act 1102 may be omitted. The process 1100 proceeds from act 1102 to act 1104.

In act 1104, the processing device simultaneously displays one of the ultrasound images depicting the longitudinal view of the object and one of the ultrasound images depicting the transverse view of the object. In some embodiments, the processing device may update the display as new ultrasound images are collected. In some embodiments, the processing device may display the ultrasound images on its own display screen. In some embodiments, the processing device may generate the ultrasound images for display on a display screen of another device. In some embodiments, the display screen may display the ultrasound images one of top of another. In some embodiments, the display screen may display the ultrasound images horizontally next to each other. Further description of displaying ultrasound images may be found with reference to FIGS. 2 and 4-9D. The process 1100 proceeds from act 1104 to act 1106.

In act 1106, the processing device receives a user selection to modify a position of an imaging plane of the ultrasound images depicting the longitudinal view of the object and/or a position of an imaging plane of the ultrasound images depicting the transverse view of the object. Further description of receiving a user selection to modify a position of an imaging plane may be found with reference to FIGS. 2 and 4-9D. In some embodiments, the processing device receives the user selection through a GUI displayed by the processing device. In some embodiments, the GUI includes an indicator of the position of the imaging plane (e.g., the transverse imaging plane indicator 232 and/or the longitudinal imaging plane indicator 236). In some embodiments, instead of or in addition to the processing device receiving a selection from a GUI to modify the location of the imaging plane, the processing device may receive a selection to modify the location of the imaging plane based on the processing device detecting a tilt of the processing device and/or based on the ultrasound device detecting a tilt of the ultrasound device. The processing device and/or the ultrasound device may detect a tilt using a motion sensor (e.g., including an accelerometer, gyroscope, and/or magnetometer).

In some embodiments, instead of or in addition to the processing device receiving a selection from a GUI to modify the location of the imaging plane, the processing device may receive a selection to modify the location of the imaging plane based on the processing device detecting one or more taps on the exterior of the ultrasound device. The ultrasound device may detect taps using tap detection circuitry, which may include a motion sensor (e.g., including an accelerometer, gyroscope, and/or magnetometer). In some embodiments, the ultrasound device may transmit an indication of the detection of the one or more taps to the processing device, which may then transmit a command to the ultrasound device to change the location of an imaging plane.

In some embodiments, instead of or in addition to the processing device receiving a selection from a GUI to modify the location of the imaging plane, the processing device may receive a selection to modify the location of the imaging plane based on the processing device receiving a voice command from a user. The processing device may receive a voice command through a speaker on the processing device.

In some embodiments, the processing device may receive the user selection to modify the location of the imaging plane without receiving a user selection to change an ultrasound imaging mode or an ultrasound imaging preset (i.e., a set of parameters optimized for imaging a particular anatomical structure or region.) The process 1100 proceeds from act 1106 to act 1108.

In act 1108, the processing device configures the ultrasound device to modify the position of the imaging plane of the ultrasound images depicting the longitudinal view of the object and/or the position of the imaging plane of the ultrasound images depicting the transverse view of the object based on the user selection. Further description of configuring the ultrasound device to modify the position of an imaging plane based on a user selection may be found with reference to FIGS. 2 and 4-9D. It should be appreciated that while the process 1100 describes ultrasound images depicting longitudinal and transverse views of an object, the same process may also be applied to ultrasound images depicting other views of an object. It should also be appreciated that the object may be an anatomical structure or feature.

In some embodiments, acts 1102 and/or 1104 may be absent. For example, the ultrasound device may collect ultrasound images having just one imaging plane, the processing device may receive a user selection to modify the position of the imaging plane, and the processing device may configure the ultrasound device to modify the position of the imaging plane based on the user selection. As another example, in some embodiments, the ultrasound device may collect ultrasound images with two imaging planes but not simultaneously display the ultrasound images.

FIG. 12 illustrates another process 1200 for biplane imaging, in accordance with certain embodiments described herein. The process 1200 is performed by a processing device in operative communication with an ultrasound device (e.g., the ultrasound device 102). For example, the processing device may be a mobile phone, tablet, or laptop. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link). The process 1200 is generally directed to configuring the ultrasound device to automatically modify the position of an ultrasound imaging plane based on the user selection. Acts 1202 and 1204 are the same as acts 1102 and 1104.

In act 1206, the processing device automatically determines whether the transverse imaging plane (i.e., the imaging plane used to collect the transverse ultrasound images) should be modified. In some embodiments, the processing device may use a statistical model to determine whether the imaging plane should be modified. For example, the statistical model may be trained to determine whether a transverse ultrasound image (e.g., the most recently collected transverse ultrasound image, generated based on ultrasound data from the ultrasound device) substantially depicts the tip of an object (e.g., a needle) or not. Substantially depicting the tip of the object may mean that the transverse ultrasound image depicts a portion of the object that is within a threshold distance of its tip. The statistical model may be trained on ultrasound images labeled with whether they substantially depict the tip of an object or not. If the processing device determines, using the statistical model, that the transverse ultrasound image does not substantially depict the tip of the object, the processing device may determine that the transverse imaging plane should be modified and the process 1200 then proceeds from act 1206 to act 1208. If the processing device determines, using the statistical model, that the transverse ultrasound image does not substantially depict the tip of the object, the processing device may determine that the transverse imaging plane should be modified and the process 1200 then remains at act 1206, in which the processing device may continue to monitor whether the transverse imaging plane should be modified.

In act 1208, the processing device configures the ultrasound device to modify the position of the transverse imaging plane. For example, the processing device may configure the ultrasound device to shift the location of the transverse imaging plane by an increment in the direction of the insertion of the needle. The process 1200 then proceeds back to act 1206, in which the processing device again determines whether the transverse imaging plane should be modified. In other words, the processing device may determine whether the shift in location of the transverse imaging plane was sufficient. For example, the processing device may again use the statistical model to determine whether transverse ultrasound images collected with the new transverse imaging plane now substantially depict the tip of the object. The processing device may be configured to automatically determine the insertion direction of the object (e.g., using a statistical model), or a user may manually input the insertion direction of the object, or the user may be instructed to insert the object in a predefined direction.

In some embodiments, acts 1202 and 1204 may be absent. For example, the ultrasound device may collect ultrasound images having just one imaging plane, the processing device may determine that the position of the imaging plane should be modified, and the processing device may configure the ultrasound device to modify the position of the imaging plane.

FIG. 13 illustrates another process 1300 for biplane imaging, in accordance with certain embodiments described herein. The process 1300 is performed by a processing device in operative communication with an ultrasound device (e.g., the ultrasound device 102). For example, the processing device may be a mobile phone, tablet, or laptop. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link). The process 1300 is generally directed to configuring the ultrasound device to automatically modify the position of the ultrasound imaging plane based on the user selection. Acts 1302 and 1304 are the same as acts 1102 and 1104.

In act 1306, the processing device configures the ultrasound device to automatically modify the location of the transverse imaging plane. In some embodiments, the processing device may configure the ultrasound device to automatically change the location of the imaging plane at a fixed speed. In some embodiments, the fixed speed may be user controllable. For example, the processing device may configure the ultrasound device to automatically change the location of the imaging plane without doing an automatic determination of the type in act 1206.

In some embodiments, acts 1302 and 1304 may be absent. For example, the ultrasound device may collect ultrasound images having just one imaging plane, the processing device may determine that the position of the imaging plane should be modified, and the processing device may configure the ultrasound device to modify the position of the imaging plane.

FIG. 14 illustrates a process 1400 for biplane imaging, in accordance with certain embodiments described herein. The process 1400 is performed by an ultrasound device (e.g., the ultrasound device 102). The process 1400 is generally directed to receiving a user selection to modify a position of an ultrasound imaging plane and moving the position of the ultrasound imaging plane based on the user selection.

In act 1402, the ultrasound device receives a user selection to modify a position of the imaging plane along the azimuthal dimension of the ultrasound device and/or a position of the imaging plane along the elevational dimension of the ultrasound device. In some embodiments, the ultrasound device may receive a selection to modify the location of the imaging plane based on the ultrasound device detecting a tilt of the ultrasound device. The ultrasound device may detect a tilt using a motion sensor (e.g., including an accelerometer, gyroscope, and/or magnetometer). In some embodiments, the ultrasound device may receive a selection to modify the location of the imaging plane based on detecting one or more taps on the exterior of the ultrasound device. The ultrasound device may detect taps using tap detection circuitry, which may include a motion sensor (e.g., including an accelerometer, gyroscope, and/or magnetometer). In some embodiments, the ultrasound device may receive a selection to modify the location of the imaging plane based on the ultrasound device receiving a voice command from a user. The ultrasound device may receive a voice command through a speaker on the ultrasound device. In some embodiments, the ultrasound device may receive the user selection to modify the location of the imaging plane without receiving a user selection to change an ultrasound imaging mode or an ultrasound imaging preset (i.e., a set of parameters optimized for imaging a particular anatomical structure or region.) The process 1400 proceeds from act 1402 to act 1404.

In act 1404, the ultrasound device modifies the position of the imaging plane along the azimuthal dimension of the ultrasound device and/or the position of the imaging plane along the elevational dimension of the ultrasound device based on the user selection. Further description of moving the position of an imaging plane based on a user selection may be found with reference to FIGS. 2 and 4-9D. It should be appreciated that while the process 1400 describes imaging planes along the azimuthal and elevational dimensions of the ultrasound device, the same process may also be applied to other imaging planes.

FIG. 15 illustrates another process 1500 for biplane imaging, in accordance with certain embodiments described herein. The process 1500 is performed by an ultrasound device (e.g., the ultrasound device 102). The process 1500 is generally directed to receiving a user selection to modify a position of an ultrasound imaging plane and moving the position of the ultrasound imaging plane based on the user selection.

In act 1502, the ultrasound device receives a user selection to modify a position of an imaging plane of the ultrasound images depicting the longitudinal view of the object and/or a position of an imaging plane of the ultrasound images depicting the transverse view of the object. In some embodiments, the ultrasound device may receive a selection to modify the location of the imaging plane based on the ultrasound device detecting a tilt of the ultrasound device. The ultrasound device may detect a tilt using a motion sensor (e.g., including an accelerometer, gyroscope, and/or magnetometer). In some embodiments, the ultrasound device may receive a selection to modify the location of the imaging plane based on detecting one or more taps on the exterior of the ultrasound device. The ultrasound device may detect taps using tap detection circuitry, which may include a motion sensor (e.g., including an accelerometer, gyroscope, and/or magnetometer). In some embodiments, the ultrasound device may receive a selection to modify the location of the imaging plane based on the ultrasound device receiving a voice command from a user. The ultrasound device may receive a voice command through a speaker on the ultrasound device. In some embodiments, the ultrasound device may receive the user selection to modify the location of the imaging plane without receiving a user selection to change an ultrasound imaging mode or an ultrasound imaging preset (i.e., a set of parameters optimized for imaging a particular anatomical structure or region.) The process 1500 proceeds from act 1502 to act 1504.

In act 1504, the ultrasound device modifies the position of the imaging plane of the ultrasound images depicting the longitudinal view of the object and/or the position of the imaging plane of the ultrasound images depicting the transverse view of the object based on the user selection. Further description of moving the position of an imaging plane based on a user selection may be found with reference to FIGS. 2 and 4-9D. It should be appreciated that while the process 1500 describes ultrasound images depicting longitudinal and transverse views of an object, the same process may also be applied to ultrasound images depicting other views of an object. It should also be appreciated that the object may be an anatomical structure or feature.

FIG. 16 illustrates another process 1600 for biplane imaging, in accordance with certain embodiments described herein. The process 1600 is performed by an ultrasound device (e.g., the ultrasound device 102). The process 1600 is generally directed to automatically moving the position of an ultrasound imaging plane based on the user selection.

In act 1602, the ultrasound device automatically determines whether the transverse imaging plane (i.e., the imaging plane used to collect the transverse ultrasound images) should be modified. In some embodiments, the ultrasound device may use a statistical model to determine whether the imaging plane should be modified. For example, the statistical model may be trained to determine whether a transverse ultrasound image (e.g., the most recently collected transverse ultrasound image, generated by the ultrasound device based on ultrasound data collected by the ultrasound device) substantially depicts the tip of an object (e.g., a needle) or not. Substantially depicting the tip of the object may mean that the transverse ultrasound image depicts a portion of the object that is within a threshold distance of its tip. The statistical model may be trained on ultrasound images labeled with whether they substantially depict the tip of an object or not. If the ultrasound device determines, using the statistical model, that the transverse ultrasound image does not substantially depict the tip of the object, the ultrasound device may determine that the transverse imaging plane should be modified and the process 1200 then proceeds from act 1606 to act 1604. If the ultrasound device determines, using the statistical model, that the transverse ultrasound image does not substantially depict the tip of the object, the ultrasound device may determine that the transverse imaging plane should be modified and the process 1600 then remains at act 1602, in which the ultrasound device may continue to monitor whether the transverse imaging plane should be modified.

In act 1604, the ultrasound device modifies the position of the transverse imaging plane. For example, the ultrasound device may configure the ultrasound device to shift the location of the transverse imaging plane by an increment in the direction of the insertion of the needle. The process 1600 then proceeds back to act 1602, in which the ultrasound device again determines whether the transverse imaging plane should be modified. In other words, the ultrasound device may determine whether the shift in location of the transverse imaging plane was sufficient. For example, the ultrasound device may again use the statistical model to determine whether transverse ultrasound images collected with the new transverse imaging plane now substantially depict the tip of the object. The ultrasound device may be configured to automatically determine the insertion direction of the object (e.g., using a statistical model), or a user may manually input the insertion direction of the object, or the user may be instructed to insert the object in a predefined direction.

In some embodiments, the ultrasound device may be configured to automatically change the location of the imaging plane at a fixed speed. For example, the ultrasound device may be configured to automatically change the location of the imaging plane without doing an automatic determination of the type in act 1602. In some embodiments, the fixed speed may be user controllable.

FIG. 17 illustrates a schematic block diagram of an example ultrasound system 1700 upon which various aspects of the technology described herein may be practiced. The ultrasound system 1700 includes an ultrasound device 1702, a processing device 1704, a network 1706, and one or more servers 1708. The processing device 1704 may be any of the processing devices described herein. The ultrasound device 1702 may be any of the ultrasound devices described herein (e.g., the ultrasound device 102).

The ultrasound device 1702 includes ultrasound circuitry 1710, processing circuitry 1724, and memory 1726. The processing device 1704 includes a camera 1720, a display screen 1712, a processor 1714, a memory 1716, an input device 1718, and a speaker 1722. The processing device 1704 is in wired (e.g., through a lightning connector or a mini-USB connector) and/or wireless communication (e.g., using BLUETOOTH, ZIGBEE, and/or WiFi wireless protocols) with the ultrasound device 1702. The processing device 1704 is in wireless communication with the one or more servers 1708 over the network 1706.

The ultrasound device 1702 may be configured to generate ultrasound data that may be employed to generate an ultrasound image. The ultrasound device 1702 may be constructed in any of a variety of ways. In some embodiments, the ultrasound device 1702 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound circuitry 1710 may be configured to generate the ultrasound data. The ultrasound circuitry 1710 may include one or more ultrasonic transducers monolithically integrated onto a single semiconductor die. The ultrasonic transducers may include, for example, one or more capacitive micromachined ultrasonic transducers (CMUTs), one or more CMOS (complementary metal-oxide-semiconductor) ultrasonic transducers (CUTs), one or more piezoelectric micromachined ultrasonic transducers (PMUTs), and/or one or more other suitable ultrasonic transducer cells. In some embodiments, the ultrasonic transducers may be formed the same chip as other electronic components in the ultrasound circuitry 1710 (e.g., transmit circuitry, receive circuitry, control circuitry, power management circuitry, and processing circuitry) to form a monolithic ultrasound device. The ultrasound device 1702 may transmit ultrasound data and/or ultrasound images to the processing device 1704 over a wired (e.g., through a lightning connector or a mini-USB connector) and/or wireless (e.g., using BLUETOOTH, ZIGBEE, and/or WiFi wireless protocols) communication link.

The processing circuitry 1724 may include specially-programmed and/or special-purpose hardware such as an application-specific integrated circuit (ASIC). The ultrasound device 1702 may be configured to perform certain of the processes (e.g., the processes 1400-1600) described herein using the processing circuitry 1724 (e.g., one or more computer hardware processors) and one or more articles of manufacture that include non-transitory computer-readable storage media such as the memory 1726. The processing circuitry 1724 may control writing data to and reading data from the memory 1726 in any suitable manner. To perform certain of the processes described herein, the processing circuitry 1724 may execute one or more processor-executable instructions stored in one or more non-transitory computer-readable storage media (e.g., the memory 1726), which may serve as non-transitory computer-readable storage media storing processor-executable instructions for execution by the processing circuitry 1724.

Referring now to the processing device 1704, the processor 1714 may include specially-programmed and/or special-purpose hardware such as an application-specific integrated circuit (ASIC). For example, the processor 1714 may include one or more graphics processing units (GPUs)

and/or one or more tensor processing units (TPUs). TPUs may be ASICs specifically designed for machine learning (e.g., deep learning). The TPUs may be employed to, for example, accelerate the inference phase of a neural network. The processing device 1704 may be configured to process the ultrasound data received from the ultrasound device 1702 to generate ultrasound images for display on the display screen 1712. The processing may be performed by, for example, the processor 1714. The processor 1714 may also be adapted to control the acquisition of ultrasound data with the ultrasound device 1702. The ultrasound data may be processed in real-time during a scanning session as the echo signals are received. In some embodiments, the displayed ultrasound image may be updated at a rate of at least 5 Hz, at least 10 Hz, at least 20 Hz, at a rate between 5 and 60 Hz, or at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

The processing device 1704 may be configured to perform certain of the processes (e.g., the processes 1000-1300) described herein using the processor 1714 (e.g., one or more computer hardware processors) and one or more articles of manufacture that include non-transitory computer-readable storage media such as the memory 1716. The processor 1714 may control writing data to and reading data from the memory 1716 in any suitable manner. To perform certain of the processes described herein, the processor 1714 may execute one or more processor-executable instructions stored in one or more non-transitory computer-readable storage media (e.g., the memory 1716), which may serve as non-transitory computer-readable storage media storing processor-executable instructions for execution by the processor 1714. The camera 1720 may be configured to detect light (e.g., visible light) to form an image. The camera 1720 may be on the same face of the processing device 1704 as the display screen 1712. The display screen 1712 may be configured to display images and/or videos, and may be, for example, a liquid crystal display (LCD), a plasma display, and/or an organic light emitting diode (OLED) display on the processing device 1704. The input device 1718 may include one or more devices capable of receiving input from a user and transmitting the input to the processor 1714. For example, the input device 1718 may include a keyboard, a mouse, a microphone, touch-enabled sensors on the display screen 1712, and/or a microphone. The display screen 1712, the input device 1718, the camera 1720, and the speaker 1722 may be communicatively coupled to the processor 1714 and/or under the control of the processor 1714.

It should be appreciated that the processing device 1704 may be implemented in any of a variety of ways. For example, the processing device 1704 may be implemented as a handheld device such as a mobile smartphone or a tablet. Thereby, a user of the ultrasound device 1702 may be able to operate the ultrasound device 1702 with one hand and hold the processing device 1704 with another hand. In other examples, the processing device 1704 may be implemented as a portable device that is not a handheld device, such as a laptop. In yet other examples, the processing device 1704 may be implemented as a stationary device such as a desktop computer. The processing device 1704 may be connected to the network 1706 over a wired connection (e.g., via an Ethernet cable) and/or a wireless connection (e.g., over a WiFi network). The processing device 1704 may thereby communicate with (e.g., transmit data to or receive data from) the one or more servers 1708 over the network 1706. For example, a party may provide from the server 1708 to the processing device 1704 processor-executable instructions for storing in one or more non-transitory computer-readable storage media (e.g., the memory 1726) which, when executed, may cause the processing device 1704 to perform certain of the processes (e.g., the processes 1000-1300) described herein. In some embodiments, the ultrasound device 1702 may also be connected to the network 1706 over a wired connection (e.g., via an Ethernet cable) and/or a wireless connection (e.g., over a WiFi network). The ultrasound device 1702 may thereby communicate with (e.g., transmit data to or receive data from) the one or more servers 1708 over the network 1706. For example, a party may provide from the server 1708 to the ultrasound device 1702 processor-executable instructions for storing in one or more non-transitory computer-readable storage media which, when executed, may cause the ultrasound device 1702 to perform certain of the processes (e.g., the processes 1400-1600) described herein. For further description of ultrasound devices and systems, see U.S. patent application Ser. No. 15/415,434 titled "UNIVERSAL ULTRASOUND DEVICE AND RELATED APPARATUS AND METHODS," filed on Jan. 25, 2017 and published as U.S. Pat. App. Publication No. 2017-0360397 A1 (and assigned to the assignee of the instant application), which is incorporated by reference herein in its entirety.

FIG. 17 should be understood to be non-limiting. For example, the ultrasound system 1700 may include fewer or more components than shown and the processing device 1704 and ultrasound device 1702 may include fewer or more components than shown. In some embodiments, the processing device 1704 may be part of the ultrasound device 1702.

Various aspects of the present disclosure may be used alone, in combination, or in a variety of arrangements not specifically precluded by the embodiments described in the foregoing, and the disclosure is therefore not limited in its application to the details and arrangement of components set forth in the foregoing text or illustrated in the drawings. For example, aspects described in one embodiment may be combined in any manner with aspects described in other embodiments.

According to an aspect of the present application, a method is provided, comprising receiving, with a processing device in operative communication with an ultrasound device, a user selection to modify a location of a first ultrasound imaging plane. The processing device is configured to receive the user selection through a graphical user interface (GUI) displayed by the processing device and including a first ultrasound imaging plane indicator. The first ultrasound imaging plane indicator indicates the location of the first ultrasound imaging plane. The method further comprises configuring the ultrasound device to modify the location of the first ultrasound imaging plane based on the user selection.

In some embodiments, receiving the user selection to modify the location of the first ultrasound imaging plane and configuring the ultrasound device to modify the location of the first ultrasound imaging plane is performed during biplane imaging. In some embodiments, receiving the user selection to modify the location of the first ultrasound imaging plane is performed without receiving a user selection to change an ultrasound imaging mode or an ultrasound imaging preset.

In some embodiments, the method further comprises configuring the ultrasound device to alternate collection of ultrasound images with the first ultrasound imaging plane and ultrasound images with a second ultrasound imaging plane.

In some embodiments, a user does not rotate the ultrasound device when the ultrasound device is alternating collection of the ultrasound images with the first ultrasound imaging plane and the ultrasound images with the second ultrasound imaging plane.

In some embodiments, the method further comprises simultaneously displaying an ultrasound image having the first ultrasound imaging plane and an ultrasound image having a second ultrasound imaging plane.

In some embodiments, the method further comprises displaying the first ultrasound imaging plane indicator superimposed on an ultrasound image with a second ultrasound imaging plane or adjacent to the ultrasound image having the second ultrasound imaging plane.

In some embodiments, the first ultrasound imaging plane indicator indicates where the first ultrasound imaging plane intersects the second ultrasound imaging plane. In some embodiments, the first ultrasound imaging plane intersects the second ultrasound imaging plane at a real-world location corresponding to a location of the first ultrasound imaging plane indicator in the ultrasound image having the second ultrasound imaging plane.

In some embodiments, receiving the user selection to modify the position of the first ultrasound imaging plane comprises detecting a dragging movement on the first ultrasound imaging plane indicator or on the ultrasound image having the second ultrasound imaging plane.

In some embodiments, receiving the user selection to modify the position of the first ultrasound imaging plane comprises receiving a selection of a location on the ultrasound image having the second ultrasound imaging plane.

In some embodiments, the method further comprises displaying a second ultrasound imaging plane indicator superimposed on the ultrasound image having the first ultrasound imaging plane or adjacent to the ultrasound image having the first ultrasound imaging plane.

In some embodiments, the second ultrasound imaging plane indicator indicates where the second ultrasound imaging plane intersects the first ultrasound imaging plane.

In some embodiments, the second ultrasound imaging plane intersects the first ultrasound imaging plane at a real-world location corresponding to a location of the second ultrasound imaging plane indicator in the ultrasound image having the first ultrasound imaging plane.

In some embodiments, the processing device does not enable a user to modify a location of the second ultrasound imaging plane. In some embodiments, the processing device does not enable a user to modify a location of the second ultrasound imaging plane, and the method further comprises displaying the first ultrasound imaging plane indicator and the second ultrasound imaging plane indicator with different formats.

In some embodiments, the method further comprises: receiving a user selection to modify a position of the second ultrasound imaging plane; and configuring the ultrasound device to modify the position of the second ultrasound imaging plane based on the user selection.

In some embodiments, the method further comprises displaying a three-dimensional visualization of the location of the first ultrasound imaging plane.

According to an aspect of the present application, an apparatus is provided, comprising: a processing device in operative communication with an ultrasound device. The processing device is configured to receive a user selection to modify a location of a first ultrasound imaging plane. The processing device may receive the user selection by detecting a tilt of the processing device, receiving, from the ultrasound device, an indication of a detection of a tilt of the ultrasound device, receiving, from the ultrasound device, an indication of a detection of one or more taps on an exterior of the ultrasound device, and/or receiving a user voice command. The processing device is further configured to configure the ultrasound device to modify the location of the first ultrasound imaging plane based on the user selection.

In some embodiments, the processing device is configured to both receive the user selection to modify the location of the first ultrasound imaging plane and to modify the location of the first ultrasound imaging plane during biplane imaging.

In some embodiments, the processing device is configured to receive the user selection to modify the location of the first ultrasound imaging plane without receiving a user selection to change an ultrasound imaging mode or an ultrasound imaging preset.

In some embodiments, the processing device is further configured to configure the ultrasound device to alternate collection of ultrasound images with the first ultrasound imaging plane and ultrasound images with a second ultrasound imaging plane.

In some embodiments, a user does not rotate the ultrasound device when the ultrasound device is alternating collection of the ultrasound images with the first ultrasound imaging plane and the ultrasound images with the second ultrasound imaging plane.

In some embodiments, the processing device does not enable a user to modify a location of the second ultrasound imaging plane.

In some embodiments, the processing device is further configured to: receive a user selection to modify a position of the second ultrasound imaging plane; and configure the ultrasound device to modify the position of the second ultrasound imaging plane based on the user selection.

According to an aspect of the present application, a method is provided, comprising: receiving, by a processing device in operative communication with an ultrasound device, a user selection to modify a location of a first ultrasound imaging plane. Receiving the user selection comprises: detecting a tilt of the processing device; receiving, from the ultrasound device, an indication of a detection of a tilt of the ultrasound device; receiving, from the ultrasound device, an indication of a detection of one or more taps on an exterior of the ultrasound device; and/or receiving a user voice command. The method further comprises configuring the ultrasound device to modify the location of the first ultrasound imaging plane based on the user selection.

In some embodiments, receiving the user selection to modify the location of the first ultrasound imaging plane and modifying the location of the first ultrasound imaging plane is performed during biplane imaging.

In some embodiments, receiving the user selection to modify the location of the first ultrasound imaging plane is performed without receiving a user selection to change an ultrasound imaging mode or an ultrasound imaging preset.

In some embodiments, the method further comprises configuring the ultrasound device to alternate collection of ultrasound images with the first ultrasound imaging plane and ultrasound images with a second ultrasound imaging plane.

In some embodiments, a user does not rotate the ultrasound device when the ultrasound device is alternating collection of the ultrasound images with the first ultrasound imaging plane and the ultrasound images with the second ultrasound imaging plane.

In some embodiments, the processing device does not enable a user to modify a location of the second ultrasound imaging plane.

In some embodiments, the method further comprises receiving a user selection to modify a position of the second ultrasound imaging plane, and configuring the ultrasound device to modify the position of the second ultrasound imaging plane based on the user selection.

According to an aspect of the present application, an apparatus is provided, comprising an ultrasound device configured to receive a user selection to modify a location of a first ultrasound imaging plane by detecting a tilt of the ultrasound device, detecting one or more taps on an exterior of the ultrasound device, and/or receiving a user voice command. The ultrasound device is further configured to modify the location of the first ultrasound imaging plane based on the user selection.

In some embodiments, the ultrasound device is configured to receive the user selection to modify the location of the first ultrasound imaging plane and to modify the location of the first ultrasound imaging plane during biplane imaging. In some embodiments, the ultrasound device is configured to receive the user selection to modify the location of the first ultrasound imaging plane without receiving a user selection to change an ultrasound imaging mode or an ultrasound imaging preset.

In some embodiments, the ultrasound device is further configured to alternate collection of ultrasound images with the first ultrasound imaging plane and ultrasound images with a second ultrasound imaging plane.

In some embodiments, a user does not rotate the ultrasound device when the ultrasound device is alternating collection of the ultrasound images with the first ultrasound imaging plane and the ultrasound images with the second ultrasound imaging plane.

In some embodiments, the ultrasound device does not enable a user to modify a location of the second ultrasound imaging plane.

In some embodiments, the ultrasound device is further configured to receive a user selection to modify a position of the second ultrasound imaging plane, and modify the position of the second ultrasound imaging plane based on the user selection.

According to an aspect of the present application, a method is provided, comprising receiving, by an ultrasound device, a user selection to modify a location of a first ultrasound imaging plane. Receiving the user selection comprises: detecting a tilt of the ultrasound device; detecting one or more taps on an exterior of the ultrasound device; and/or receiving a user voice command. The method further comprises modifying the location of the first ultrasound imaging plane based on the user selection.

In some embodiments, receiving the user selection to modify the location of the first ultrasound imaging plane and modifying the location of the first ultrasound imaging plane is performed during biplane imaging. In some embodiments, receiving the user selection to modify the location of the first ultrasound imaging plane is performed without receiving a user selection to change an ultrasound imaging mode or an ultrasound imaging preset.

In some embodiments, the method further comprises alternating collection of ultrasound images with the first ultrasound imaging plane and ultrasound images with a second ultrasound imaging plane.

In some embodiments, a user does not rotate the ultrasound device when the ultrasound device is alternating collection of the ultrasound images with the first ultrasound imaging plane and the ultrasound images with the second ultrasound imaging plane.

In some embodiments, the ultrasound device does not enable a user to modify a location of the second ultrasound imaging plane.

In some embodiments, the method further comprises: receiving a user selection to modify a position of the second ultrasound imaging plane; and modifying the position of the second ultrasound imaging plane based on the user selection.

According to an aspect of the present application, an apparatus is provided, comprising a processing device in operative communication with an ultrasound device, the processing device configured to configure the ultrasound device to automatically modify the location of an ultrasound imaging plane.

In some embodiments, the processing device is configured to configure the ultrasound device to automatically modify the location of the ultrasound imaging plane during biplane imaging.

In some embodiments, the processing device is further configured to automatically determine whether the ultrasound imaging plane should be modified, and the processing device is configured to configure the ultrasound device to automatically modify the location of the ultrasound imaging plane based on automatically determining whether the ultrasound imaging plane should be modified.

In some embodiments, the processing device is configured, when automatically determining whether the ultrasound imaging plane should be modified, to use a statistical model to determine whether the imaging plane should be modified.

In some embodiments, the processing device is configured, when using the statistical model to determine whether the imaging plane should be modified, to determine whether an ultrasound image substantially depicts a tip of an object.

In some embodiments, the processing device is configured, when configuring the ultrasound device to automatically modify the location of the ultrasound imaging plane, to shift the location of the ultrasound imaging plane by an increment in a direction of an insertion of the object.

In some embodiments, the ultrasound image depicts a transverse view of the object. In some embodiments, the processing device is further configured to automatically determine the direction of the insertion of the object. In some embodiments, the processing device is further configured to receive an input of the direction of the insertion of the object from a user.

In some embodiments, the processing device is configured, when configuring the ultrasound device to automatically modify the location of the ultrasound imaging plane, to configure the ultrasound device to automatically modify the location of the ultrasound imaging plane at a fixed speed.

According to an aspect of the present application, a method is provided, comprising configuring, by a processing device in operative communication with an ultrasound device, the ultrasound device to automatically modify the location of an ultrasound imaging plane.

In some embodiments, configuring the ultrasound device to automatically modify the location of the ultrasound imaging plane is performed during biplane imaging.

In some embodiments, the method further comprises automatically determining whether the ultrasound imaging plane should be modified. Configuring the ultrasound device to automatically modify the location of the ultrasound imaging plane is based on automatically determining whether the ultrasound imaging plane should be modified.

In some embodiments, automatically determining whether the ultrasound imaging plane should be modified comprises using a statistical model to determine whether the imaging plane should be modified. In some embodiments, using the statistical model to determine whether the imaging plane should be modified comprises determining whether an ultrasound image substantially depicts a tip of an object. In some embodiments, configuring the ultrasound device to automatically modify the location of the ultrasound imaging plane comprises shifting the location of the ultrasound imaging plane by an increment in a direction of insertion of the object.

In some embodiments, the ultrasound image depicts a transverse view of the object.

In some embodiments, the method further comprises automatically determining the direction of the insertion of the object.

In some embodiments, the method further comprises receiving an input of the direction of the insertion of the object from a user.

In some embodiments, configuring the ultrasound device to automatically modify the location of the ultrasound imaging plane comprises configuring the ultrasound device to automatically modify the location of the ultrasound imaging plane at a fixed speed.

According to an aspect of the present application, an apparatus is provided, comprising an ultrasound device configured to automatically modify a location of an ultrasound imaging plane.

In some embodiments, the ultrasound device is configured to automatically modify the location of the ultrasound imaging plane during biplane imaging.

In some embodiments, the ultrasound device is further configured to automatically determine whether the ultrasound imaging plane should be modified, and the ultrasound device is configured to automatically modify the location of the ultrasound imaging plane based on automatically determining whether the ultrasound imaging plane should be modified.

In some embodiments, the ultrasound device is configured, when automatically determining whether the ultrasound imaging plane should be modified, to use a statistical model to determine whether the imaging plane should be modified.

In some embodiments, the ultrasound device is configured, when using the statistical model to determine whether the imaging plane should be modified, to determine whether an ultrasound image substantially depicts a tip of an object.

In some embodiments, the ultrasound device is configured, when automatically modifying the location of the ultrasound imaging plane, to shift the location of the ultrasound imaging plane by an increment in a direction of an insertion of the object.

In some embodiments, the ultrasound image depicts a transverse view of the object.

In some embodiments, the ultrasound device is further configured to automatically determine the direction of the insertion of the object.

In some embodiments, the ultrasound device is further configured to receive an input of the direction of the insertion of the object from a user.

In some embodiments, the ultrasound device is configured, when automatically modifying the location of the ultrasound imaging plane, to automatically modify the location of the ultrasound imaging plane at a fixed speed.

According to an aspect of the present application, a method is provided, comprising automatically modifying, by an ultrasound device, a location of an ultrasound imaging plane.

In some embodiments, automatically modifying the location of the ultrasound imaging plane is performed during biplane imaging.

In some embodiments, the method further comprises automatically determining whether the ultrasound imaging plane should be modified, and automatically modifying the location of the ultrasound imaging plane is based on automatically determining whether the ultrasound imaging plane should be modified.

In some embodiments, automatically determining whether the ultrasound imaging plane should be modified comprises using a statistical model to determine whether the imaging plane should be modified.

In some embodiments, using the statistical model to determine whether the imaging plane should be modified comprises determining whether an ultrasound image substantially depicts a tip of an object.

In some embodiments, automatically modifying the location of the ultrasound imaging plane comprises shifting the location of the ultrasound imaging plane by an increment in a direction of insertion of the object.

In some embodiments, the ultrasound image depicts a transverse view of the object.

In some embodiments, the method further comprises automatically determining the direction of the insertion of the object.

In some embodiments, the method further comprises receiving an input of the direction of the insertion of the object from a user.

In some embodiments, automatically modifying the location of the ultrasound imaging plane comprises automatically modifying the location of the ultrasound imaging plane at a fixed speed.

In any of the foregoing embodiments, the object may be a needle unless otherwise indicated.

In any of the foregoing embodiments involving first and second ultrasound imaging planes, the second ultrasound imaging plane may be along an elevational dimension of the ultrasound device or the azimuthal dimension. The first ultrasound imaging plane may be along the azimuthal dimension of the ultrasound device or the elevational dimension.

In any of the foregoing embodiments involving alternating collection of the ultrasound images with the first ultrasound imaging plane and the ultrasound images with the second ultrasound imaging plane, the method may comprise or the processing device may be configured to configure the ultrasound device to collect ultrasound images such that a time period between collection of successive ultrasound images is in the range of approximately $\frac{1}{30}$-$\frac{1}{15}$ seconds. In any of the foregoing embodiments involving alternating collection of the ultrasound images with the first ultrasound imaging plane and the ultrasound images with the second ultrasound imaging plane, the method may comprise or the processing device may be configured to configure the ultrasound device to collect one ultrasound image having the first ultrasound imaging plane, then collect one ultrasound image having the second ultrasound imaging plane, and then collect one ultrasound image having the first ultrasound imaging plane. In any of the foregoing embodiments involving alternating collection of the ultrasound images with the first ultrasound imaging plane and the ultrasound images with the second ultrasound imaging plane, the method may comprise or the processing device may be configured to configure the ultrasound device to collect one or more ultrasound images with the first ultrasound imaging plane, then collect one or more ultrasound images with the second ultrasound imaging plane, then collect one or more ultrasound images with the first ultrasound imaging plane. In any of the foregoing embodiments involving alternating collection of the ultrasound images with the first ultrasound imaging plane and the ultrasound images with the second ultrasound imaging plane, the method may comprise or the processing device may be configured to configure the ultrasound device to collect the ultrasound images with the first ultrasound imaging plane using a first aperture and to collect the ultrasound images with the second ultrasound imaging plane using a second aperture. In some such embodiments, the first ultrasound imaging plane is along an elevational dimension of the ultrasound device, the second ultrasound imaging plane is along an azimuthal dimension of the ultrasound device, the first aperture has a long dimension along the elevational dimension of the ultrasound device, and the second aperture has a long dimension along the azimuthal dimension of the ultrasound device. In any of the foregoing embodiments involving alternating collection of the ultrasound images with the first ultrasound imaging plane and the ultrasound images with the second ultrasound imaging plane, the method may comprise or the processing device may be configured to configure the ultrasound device to collect the ultrasound images with the first ultrasound imaging plane using a first set of beamforming parameters and to collect the ultrasound images with the second ultrasound imaging plane using a second set of beamforming parameters.

In any of the foregoing embodiments involving a fixed speed for automatically modifying a location of an ultrasound imaging plane, the fixed speed may be user-controllable.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound system, comprising:
a smartphone or tablet in operative communication with an ultrasound device, wherein the smartphone or tablet is configured to:
receive, from the ultrasound device, a longitudinal ultrasound image collected with a longitudinal ultrasound imaging plane and a transverse ultrasound image collected with a transverse ultrasound imaging plane, wherein the longitudinal ultrasound imaging plane is longitudinal to a vessel and the transverse ultrasound imaging plane is transverse to the vessel;
operate an ultrasound transducer array to alternatively have a first subset of ultrasound transducers form a first aperture to collect ultrasound images with the longitudinal ultrasound imaging plane and have a second subset of ultrasound transducers form a second aperture to collect ultrasound images with the transverse ultrasound imaging plane,
simultaneously display, on a graphical user interface (GUI) of the smartphone or tablet:
the longitudinal ultrasound image;
the transverse ultrasound image, wherein the transverse ultrasound image comprises a first imaging plane identifier line; and
a transverse imaging plane visualization superimposed on the longitudinal ultrasound image and comprising a second imaging plane identifier line; wherein:

the second imaging plane identifier is sized as to reveal substantially the longitudinal ultrasound image, and wherein
the transverse imaging plane visualization illustrates a slice through the longitudinal ultrasound image representing a location of the transverse ultrasound imaging plane; and
a location of the second imaging plane identifier line corresponds to a location of the first imaging plane identifier line, such that regions of the transverse ultrasound image depicted adjacent to the first imaging plane identifier line were collected from regions of the transverse imaging plane depicted adjacent to the second imaging plane identifier line of the transverse imaging plane visualization;
receive a user selection to modify a location of the transverse ultrasound imaging plane; and
configure the ultrasound device with a configuration to modify the location of the transverse ultrasound imaging plane based on the user selection; and the ultrasound device, wherein the ultrasound device is configured to:
receive the configuration from the smartphone or tablet and modify the location of the transverse ultrasound imaging plane based on the configuration by changing between a plurality of apertures of the ultrasound device and/or by changing beamforming parameters of the ultrasound device,
wherein the ultrasound device is configured, when modifying the location of the transverse ultrasound imaging plane based on the configuration by changing between the plurality of apertures of the ultrasound device and/or by changing the beamforming parameters of the ultrasound device, to translate the transverse ultrasound imaging plane when an imaging depth of detection is less than a first threshold depth value and tilt the transverse ultrasound imaging plane when the imaging depth of detection is greater than the first threshold depth value.

2. The ultrasound system of claim 1, wherein the smartphone or tablet is configured to receive the user selection to modify the location of the transverse ultrasound imaging plane without receiving a user selection to change an ultrasound imaging mode or an ultrasound imaging preset.

3. The ultrasound system of claim 1, wherein the smartphone or tablet is configured, when configuring the ultrasound device to alternate collection of the ultrasound images with the longitudinal ultrasound imaging plane and the ultrasound images with the transverse ultrasound imaging plane, to:
configure the ultrasound device to collect ultrasound images such that a time period between collection of successive ultrasound images is in a range of approximately ⅟30-⅟15 seconds.

4. The ultrasound system of claim 1, wherein:
the longitudinal ultrasound imaging plane is along an elevational dimension of the ultrasound device;
the transverse ultrasound imaging plane is along an azimuthal dimension of the ultrasound device;
the first aperture has a long dimension along the elevational dimension of the ultrasound device; and
the second aperture has a long dimension along the azimuthal dimension of the ultrasound device.

5. The ultrasound system of claim 1, wherein the smartphone or tablet is configured, when configuring the ultrasound device to alternate collection of the ultrasound images with the longitudinal ultrasound imaging plane and the ultrasound images with the transverse ultrasound imaging plane, to:

configure the ultrasound device to collect the ultrasound images with the longitudinal ultrasound imaging plane using a first set of beamforming parameters and to collect the ultrasound images with the second ultrasound imaging plane using a second set of beamforming parameters.

6. The ultrasound system of claim 1, wherein a user does not rotate the ultrasound device when the ultrasound device is alternating collection of the ultrasound images with the longitudinal ultrasound imaging plane and the ultrasound images with the second transverse ultrasound imaging plane.

7. The ultrasound system of claim 1, wherein the smartphone or tablet is configured, when receiving the user selection to modify the position of the transverse ultrasound imaging plane, to detect a user dragging movement on the GUI of the smartphone or tablet.

8. The ultrasound system of claim 1, wherein the smartphone or tablet is configured, when receiving the user selection to modify the position of the transverse ultrasound imaging plane, to receive a selection of a location on the longitudinal ultrasound image.

9. The ultrasound system of claim 1, wherein the smartphone or tablet is further configured to display a longitudinal ultrasound imaging plane indicator superimposed on the transverse ultrasound image or adjacent to the transverse ultrasound image.

10. The ultrasound system of claim 9, wherein the longitudinal ultrasound imaging plane indicator indicates where the longitudinal ultrasound imaging plane intersects the transverse ultrasound imaging plane.

11. The ultrasound system of claim 10, wherein the longitudinal ultrasound imaging plane intersects the transverse ultrasound imaging plane at a real-world location corresponding to a location of the longitudinal ultrasound imaging plane indicator in the transverse ultrasound image.

12. The ultrasound system of claim 1, wherein the smartphone or tablet is further configured to display a freedom-of-movement indicator depicting a range of possible positions for the transverse ultrasound imaging plane.

13. The ultrasound system of claim 1, wherein the transverse imaging plane visualization comprises a three-dimensional visualization.

14. The ultrasound system of claim 1, wherein the smartphone or tablet is configured to display the transverse imaging plane visualization in response to a user interaction with the GUI of the smartphone or tablet.

15. The ultrasound system of claim 1, wherein the smartphone or tablet is further configured to cause the transverse imaging plane visualization to persist for a period of time and then disappear.

16. The ultrasound system of claim 1, wherein the smartphone or tablet is further configured to switch an orientation of the transverse ultrasound image relative to the transverse ultrasound imaging plane in response to a user selection.

17. The ultrasound system of claim 1, wherein the transverse imaging plane visualization comprises a square-like shape or a sector-like shape.

\*    \*    \*    \*    \*